US012707895B2

United States Patent
(12) United States Patent
Lee et al.

(10) Patent No.: US 12,707,895 B2
(45) Date of Patent: Aug. 11, 2026

(54) METHODS AND SYSTEMS FOR A MODIFIED BACKING

(71) Applicant: GE Precision Healthcare LLC, Wauwatosa, WI (US)

(72) Inventors: Warren Lee, Niskayuna, NY (US); Caitlin Theresa Strobel, New Castle, PA (US); Jaroslaw Kurzac, Waukesha, WI (US); James J. Van Bogart, Waukesha, WI (US); Yanju Wang, Waukesha, WI (US); Kwok Pong Chan, Niskayuna, NY (US); Chi Tat Chiu, Niskayuna, NY (US); Timothy J Fiorillo, Niskayuna, NY (US); Jimmie A Beacham, Waukesha, WI (US)

(73) Assignee: GE PRECISION HEALTHCARE LLC, Wauwatosa, WI (US)

( * ) Notice: Subject to any disclaimer, the term of this patent is extended or adjusted under 35 U.S.C. 154(b) by 404 days.

(21) Appl. No.: 18/309,344

(22) Filed: Apr. 28, 2023

(65) Prior Publication Data

US 2024/0365671 A1 Oct. 31, 2024

(51) Int. Cl.

| | |
|---|---|
| ***H10N 30/80*** | (2023.01) |
| ***A61B 8/00*** | (2006.01) |
| ***B06B 1/06*** | (2006.01) |
| ***B33Y 10/00*** | (2015.01) |
| ***B33Y 80/00*** | (2015.01) |

(52) U.S. Cl.

CPC ............. *H10N 30/80* (2023.02); *A61B 8/546* (2013.01); *B06B 1/0644* (2013.01); *B33Y 10/00* (2014.12); *B33Y 80/00* (2014.12)

(58) Field of Classification Search

CPC .. B22F 10/20; B22F 10/60; B22F 3/26; B22F 7/00; B22F 1/145; B22F 7/06; B22F 7/002; B22F 3/1109; B22F 3/1134; B22F 10/28; B33Y 10/00; B33Y 80/00; B33Y 70/10; B33Y 40/10; A61B 8/445; A61B 8/4455; A61B 8/4483; A61B 8/546; A61B 8/4444; B06B 1/0644; B06B 1/0685; H10N 30/80; B29C 64/153

See application file for complete search history.

(56) References Cited

U.S. PATENT DOCUMENTS

| | | | | |
|---|---|---|---|---|
| 2005/0075571 | A1* | 4/2005 | Barnes | G10K 11/002 600/459 |
| 2013/0345567 | A1* | 12/2013 | Sudol | B06B 1/0629 600/459 |
| 2017/0239726 | A1* | 8/2017 | Palumbo | B01D 39/14 |
| 2022/0000451 | A1* | 1/2022 | Bryzek | B06B 1/0622 |
| 2024/0173017 | A1* | 5/2024 | Manning | A61B 8/4483 |

OTHER PUBLICATIONS

"HTC Graphite," Entegris POCO Materials Website, Available Online at https://poco.entegris.com/en/home/products/premium-graphite/thermal-management-materials/htc.html, Available as Early as Aug. 6, 2020, 2 pages.

* cited by examiner

*Primary Examiner* — Abdallah Abulaban
*Assistant Examiner* — Amie M Ndure
(74) *Attorney, Agent, or Firm* — McCoy Russell LLP

(57) ABSTRACT

Various methods and systems are provided for a probe for a medical device. In one example, the probe includes an additively manufactured backing having a porous matrix and one or more thermal management structures. The porous matrix may attenuate acoustic energy and the one or more thermal management structures may enable a transfer of heat from a front of the probe to a rear of the probe.

10 Claims, 17 Drawing Sheets

METHODS AND SYSTEMS FOR A MODIFIED BACKING

FIELD

Embodiments of the subject matter disclosed herein relate to a transducer probe for a medical device.

BACKGROUND

Transducer probes are used in a variety of applications to convert energy from a physical form to an electrical form. For example, a transducer probe may include piezoelectric materials which may vibrate at a resonance frequency when a mechanical stress or strain is exerted on the materials. An acoustic signal may be generated by the vibrating piezoelectric materials which may be transmitted from a front end of the transducer probe. In order to absorb and attenuate acoustic energy scattered in directions away from the front end of the transducer probe, such as towards a rear end of the transducer probe, a backing may be included in an acoustic stack of the transducer probe. The backing may be arranged behind the piezoelectric materials, relative to a direction of signal propagation, and may be formed of materials that dampen the scattered acoustic energy, thereby reducing reverberation of the acoustic energy and mitigating interference with signal reception at the transducer probe.

BRIEF DESCRIPTION

In one embodiment, a probe includes an additively manufactured backing having a porous matrix and one or more thermal management structures. The porous matrix may attenuate acoustic energy and the one or more thermal management structures may enable a transfer of heat from a front of the probe to a rear of the probe. As a result, the backing may be readily optimized according to a specific probe type and application and reduce a cost and complexity of manufacturing.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

Figure 1:
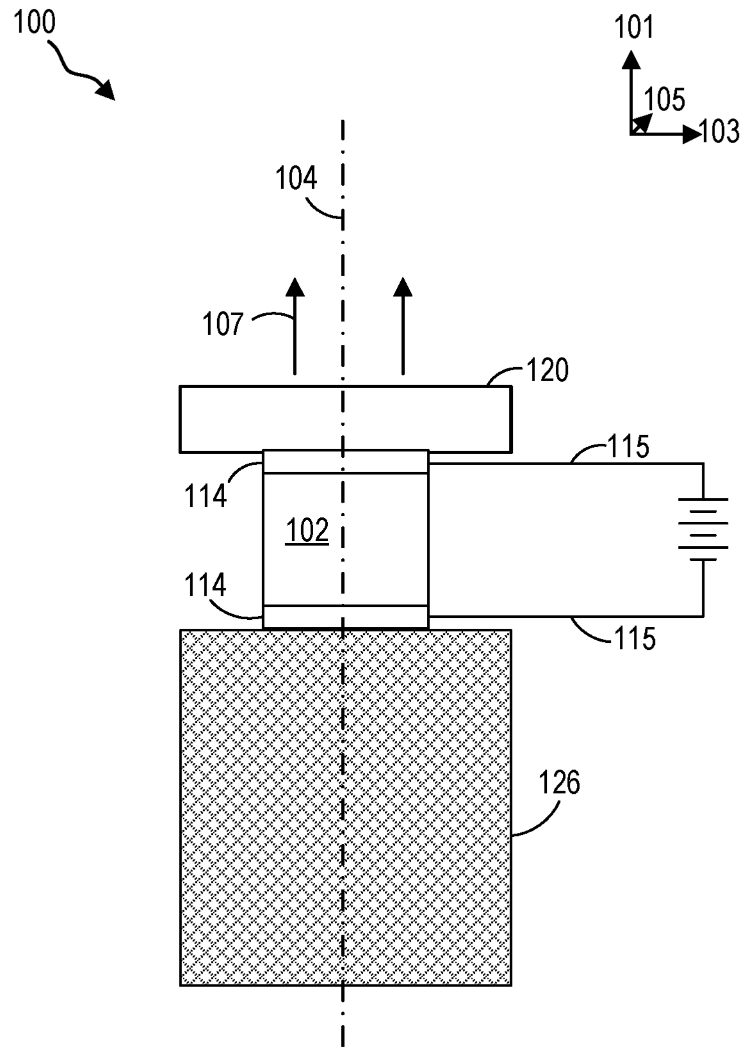
FIG. 1 shows an acoustic stack of an ultrasound transducer which may include a modified backing, according to an embodiment.
Figure 2:
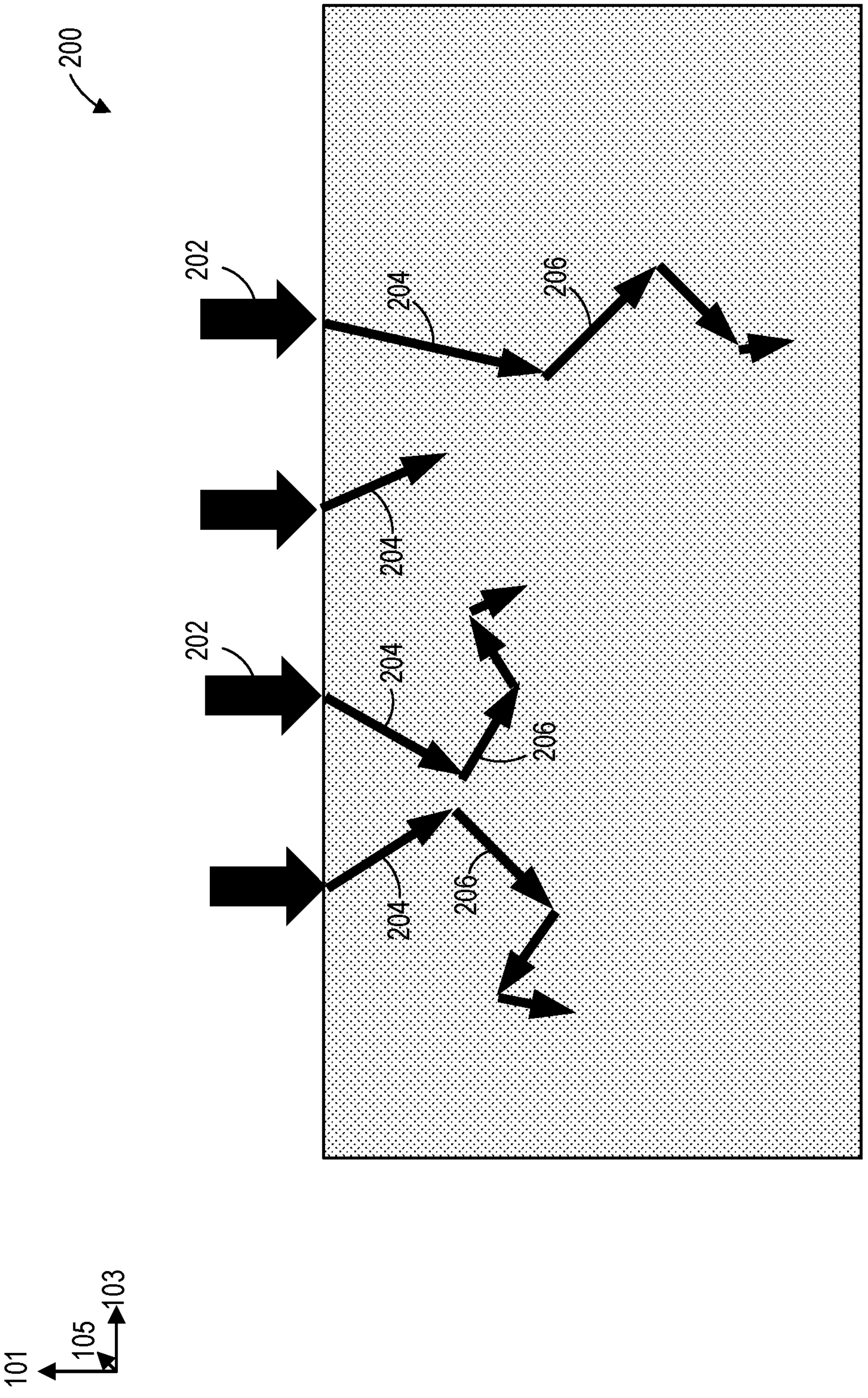
FIG. 2 shows an illustration of attenuation of acoustic energy in a modified backing, according to an embodiment.
Figure 3:
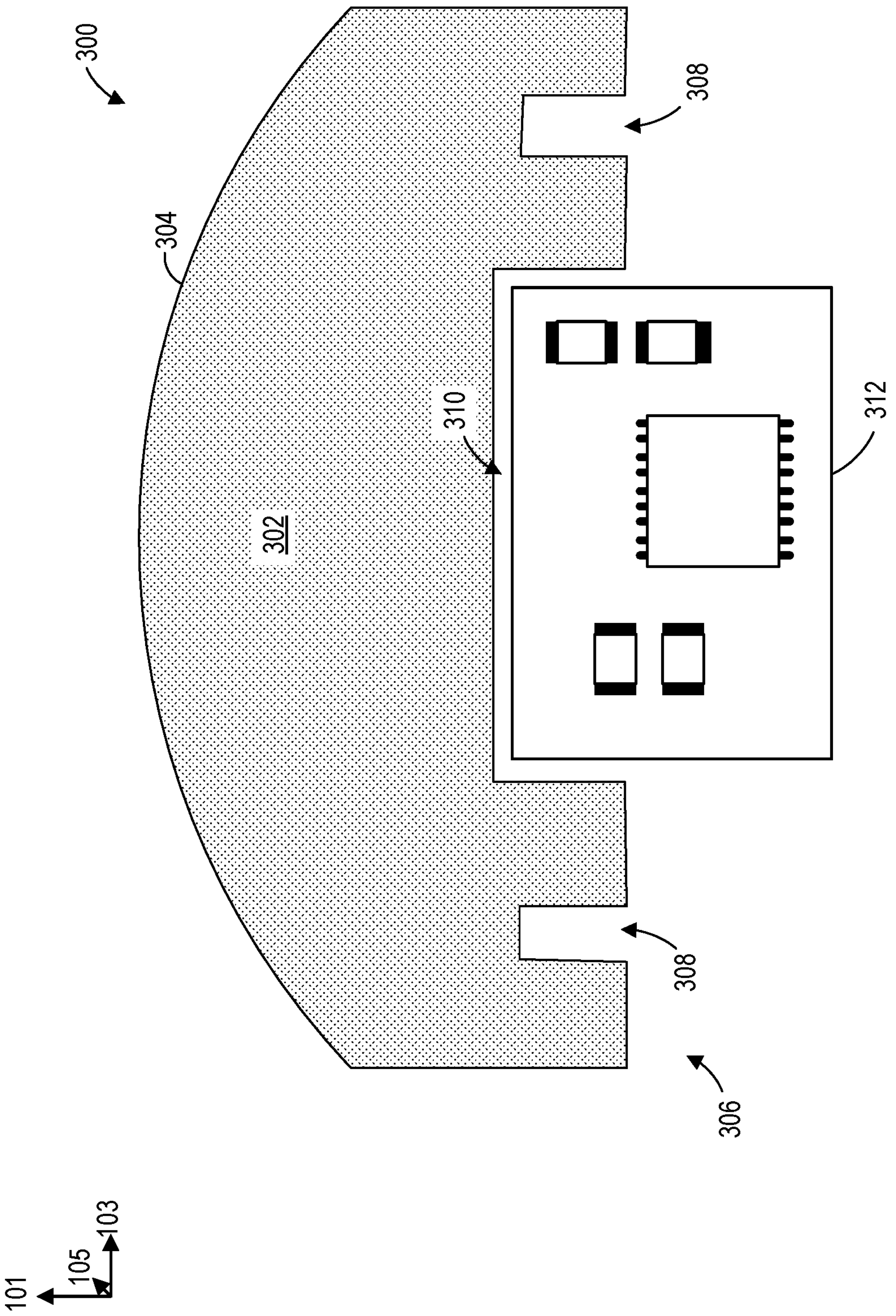
FIG. 3 shows a modified backing having a curved geometry, according to an embodiment.
Figure 4:
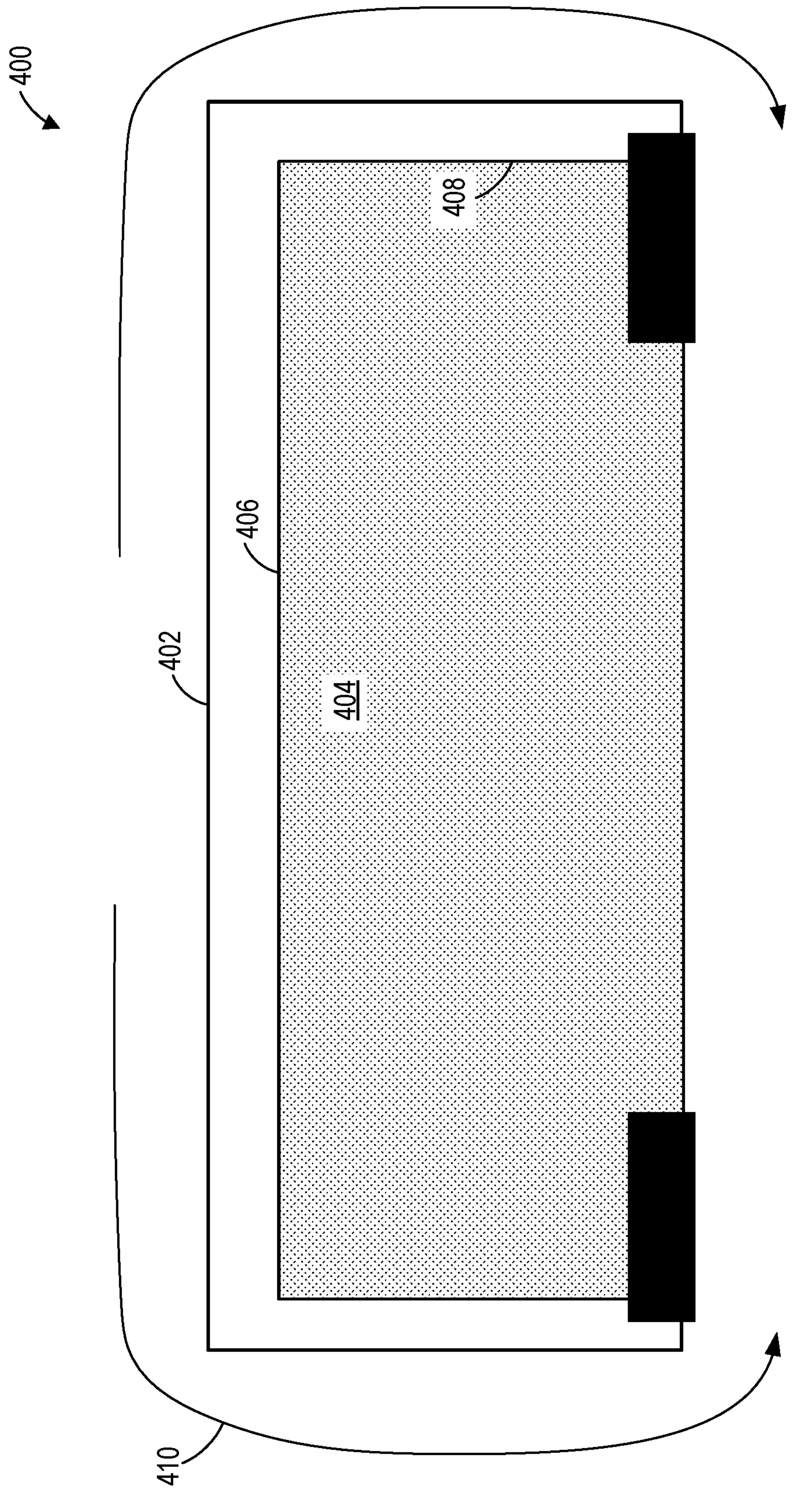
FIG. 4 shows a modified backing surrounded by an external wall, according to an embodiment.
Figure 5:
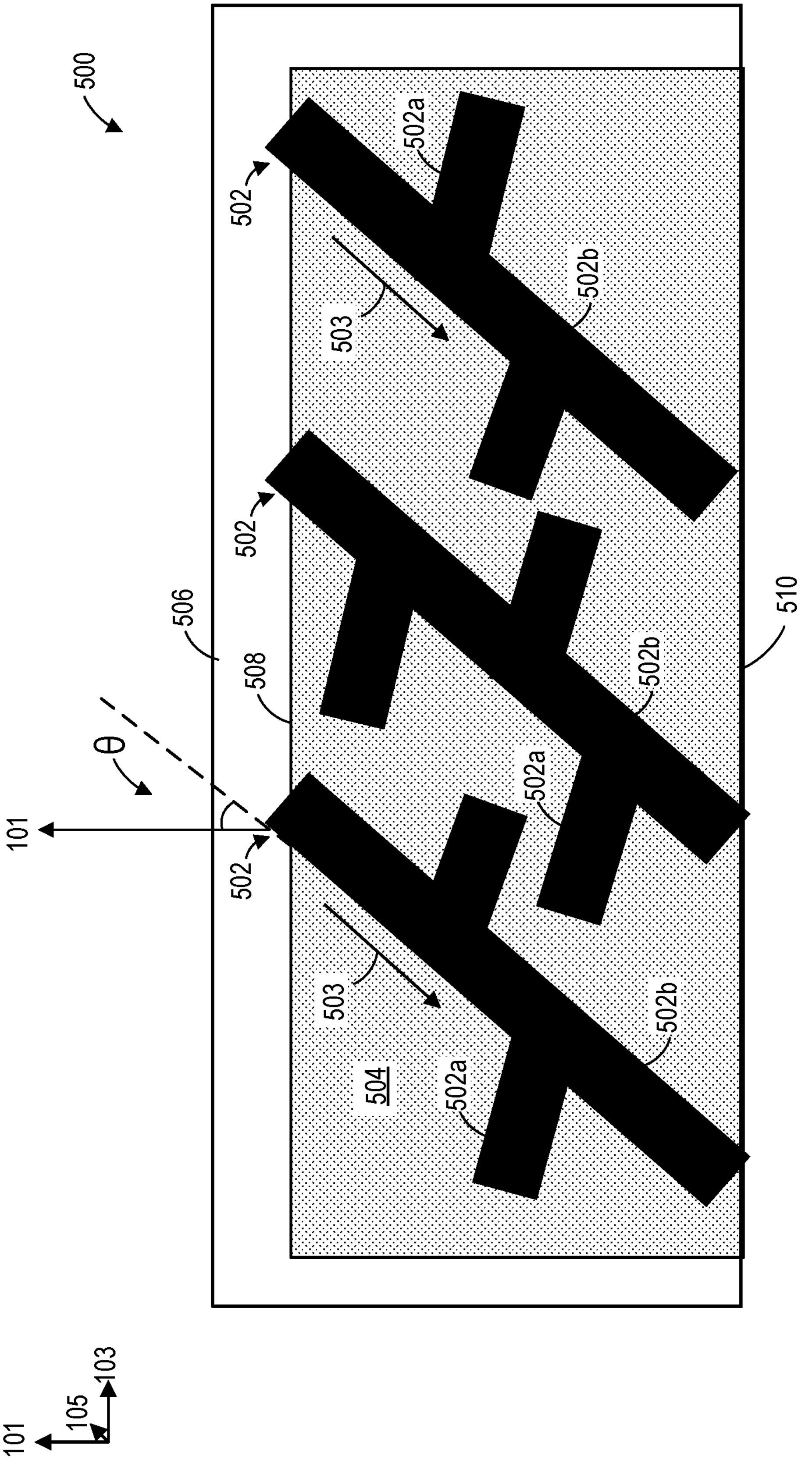
FIG. 5 shows a modified backing with a first example of internal inclusions, according to an embodiment.
Figure 6:
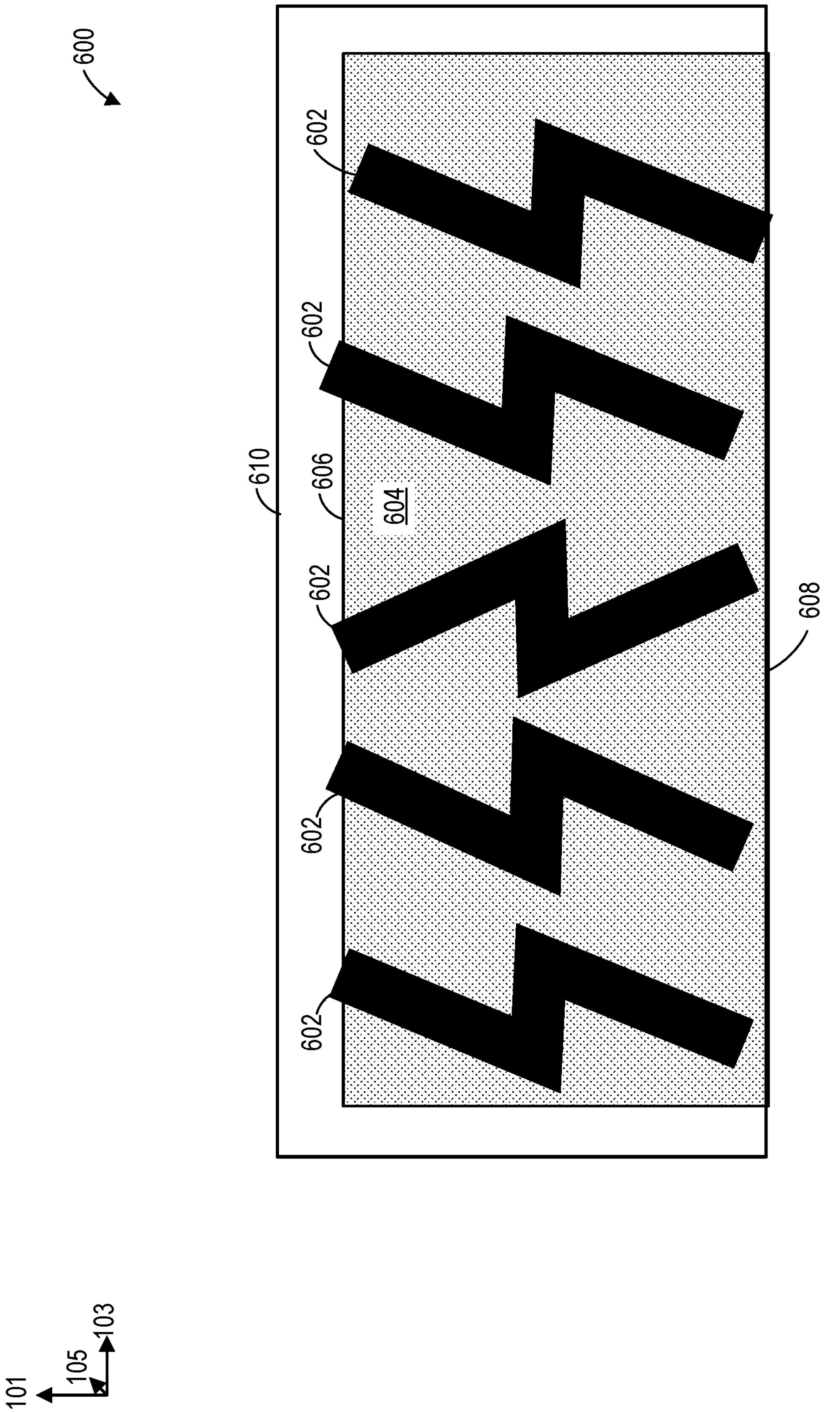
FIG. 6 shows a modified backing with a second example of internal inclusions, according to an embodiment.
Figure 7:
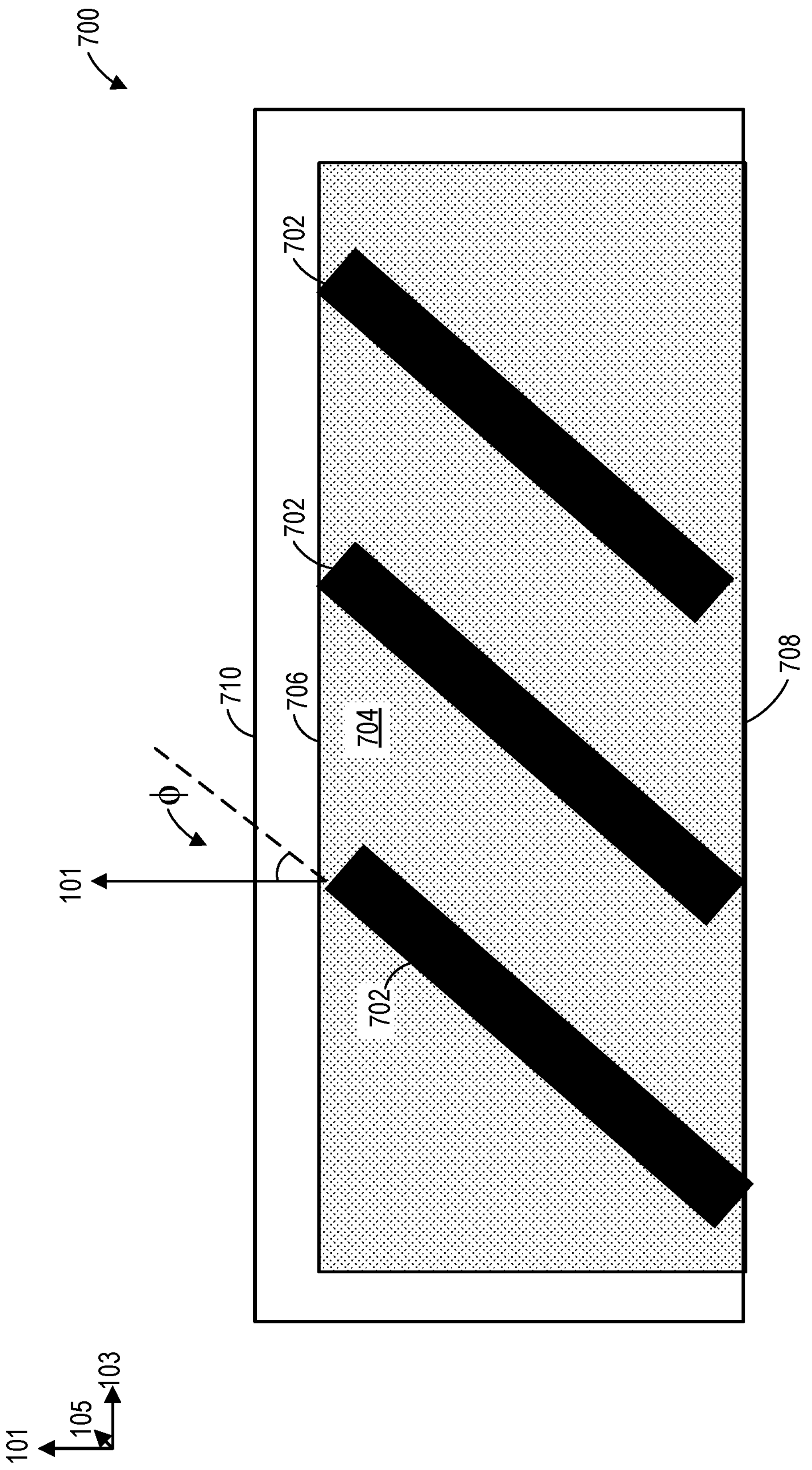
FIG. 7 shows a modified backing with a third example of internal inclusions, according to an embodiment.
Figure 8:
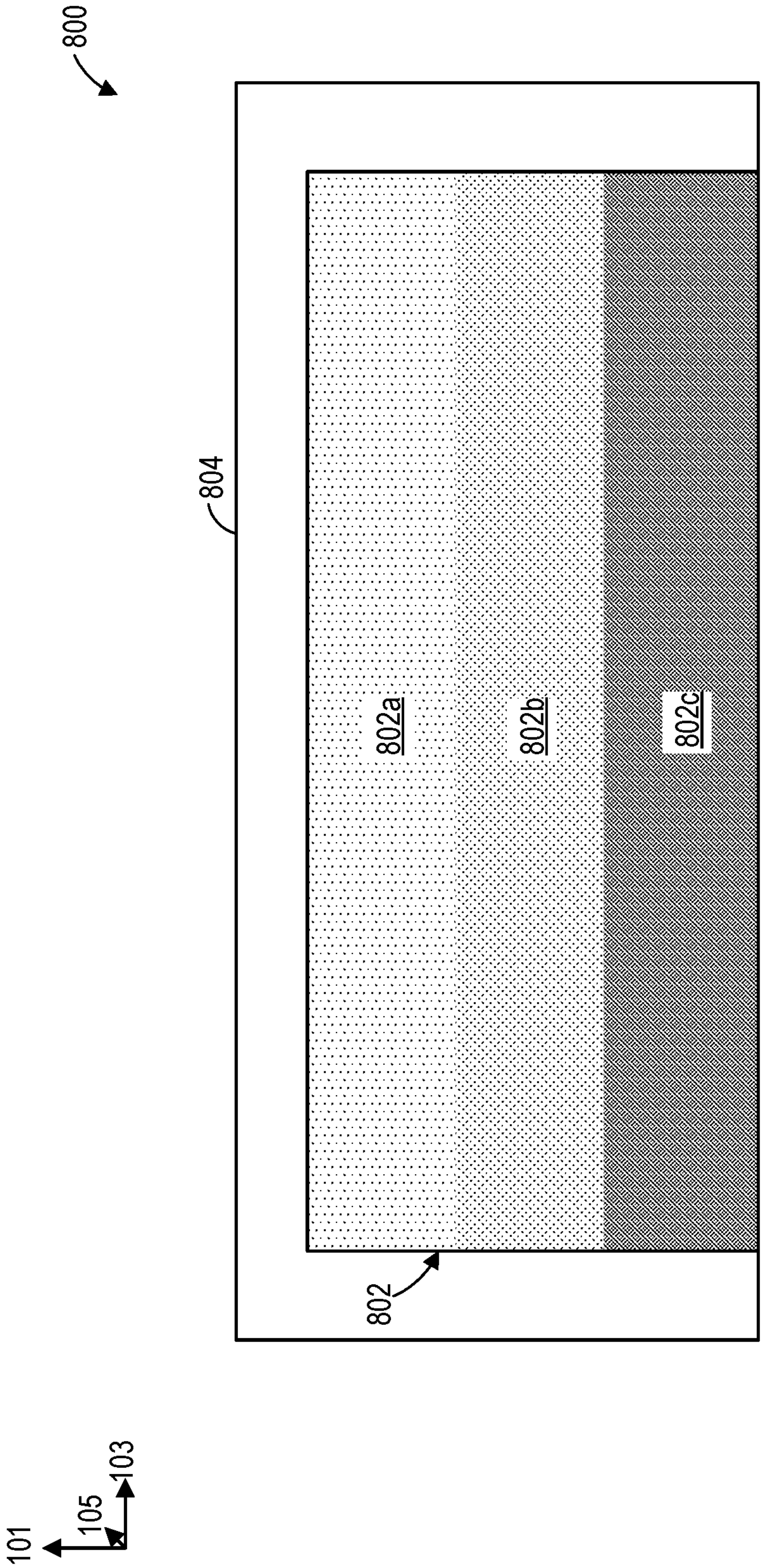
FIG. 8 shows a modified backing having a gradient structure, according to an embodiment.
Figure 9:
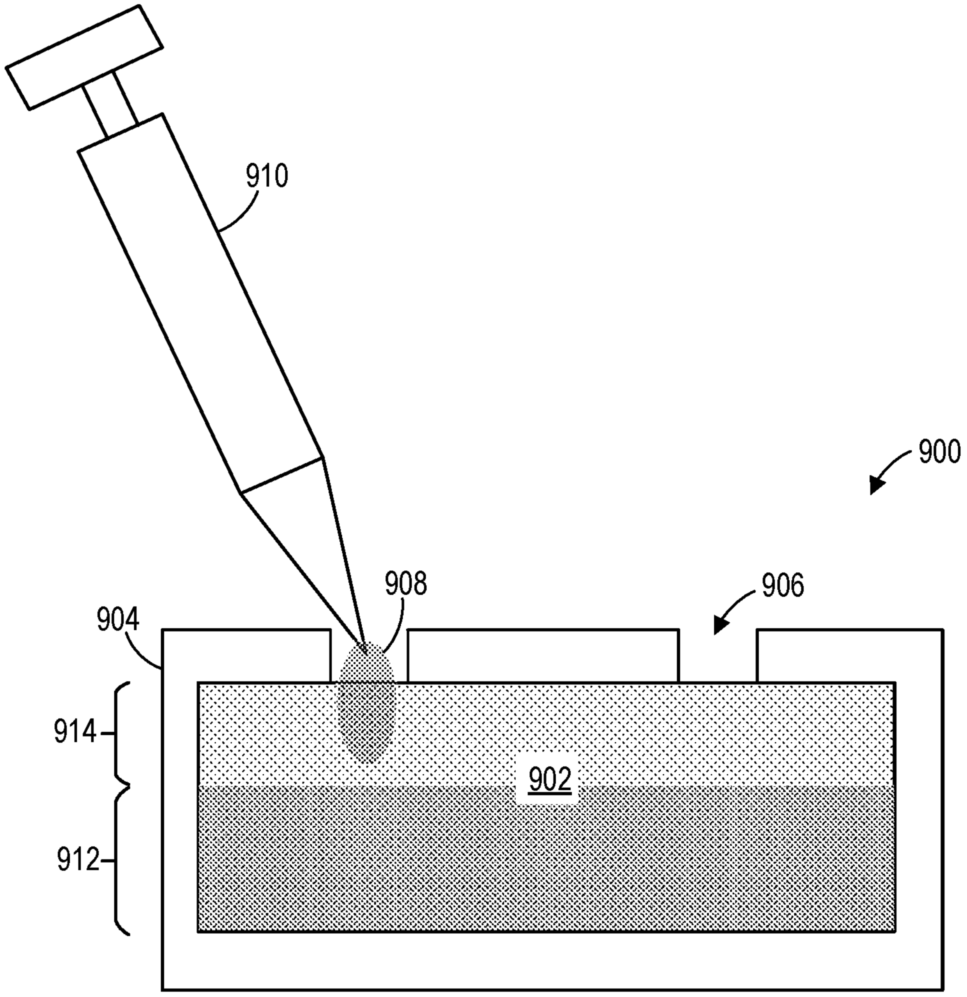
FIG. 9 shows injection of a filler into a modified backing, according to an embodiment.
Figure 10:
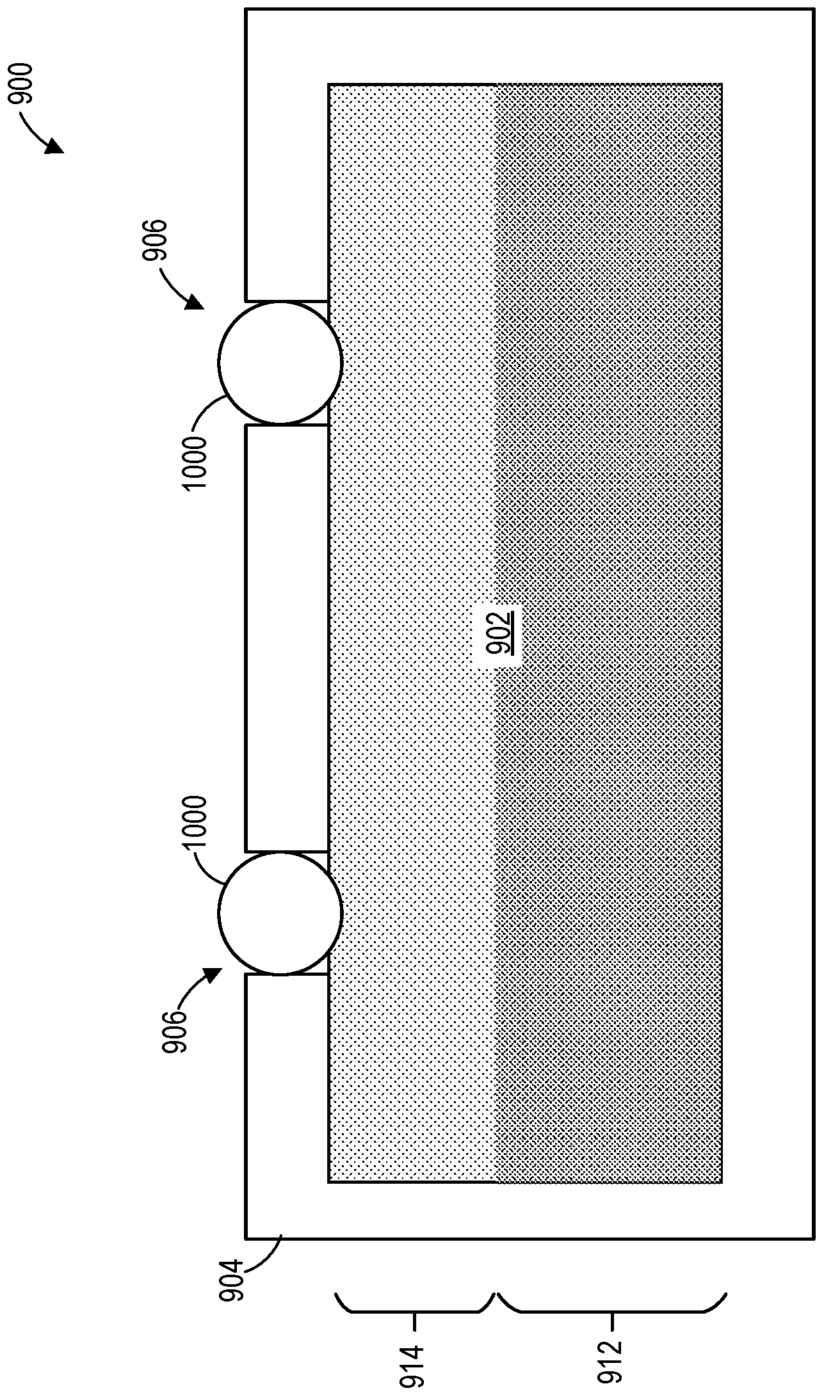
FIG. 10 shows a sealed modified backing injected with a filler, according to an embodiment.
Figure 15:
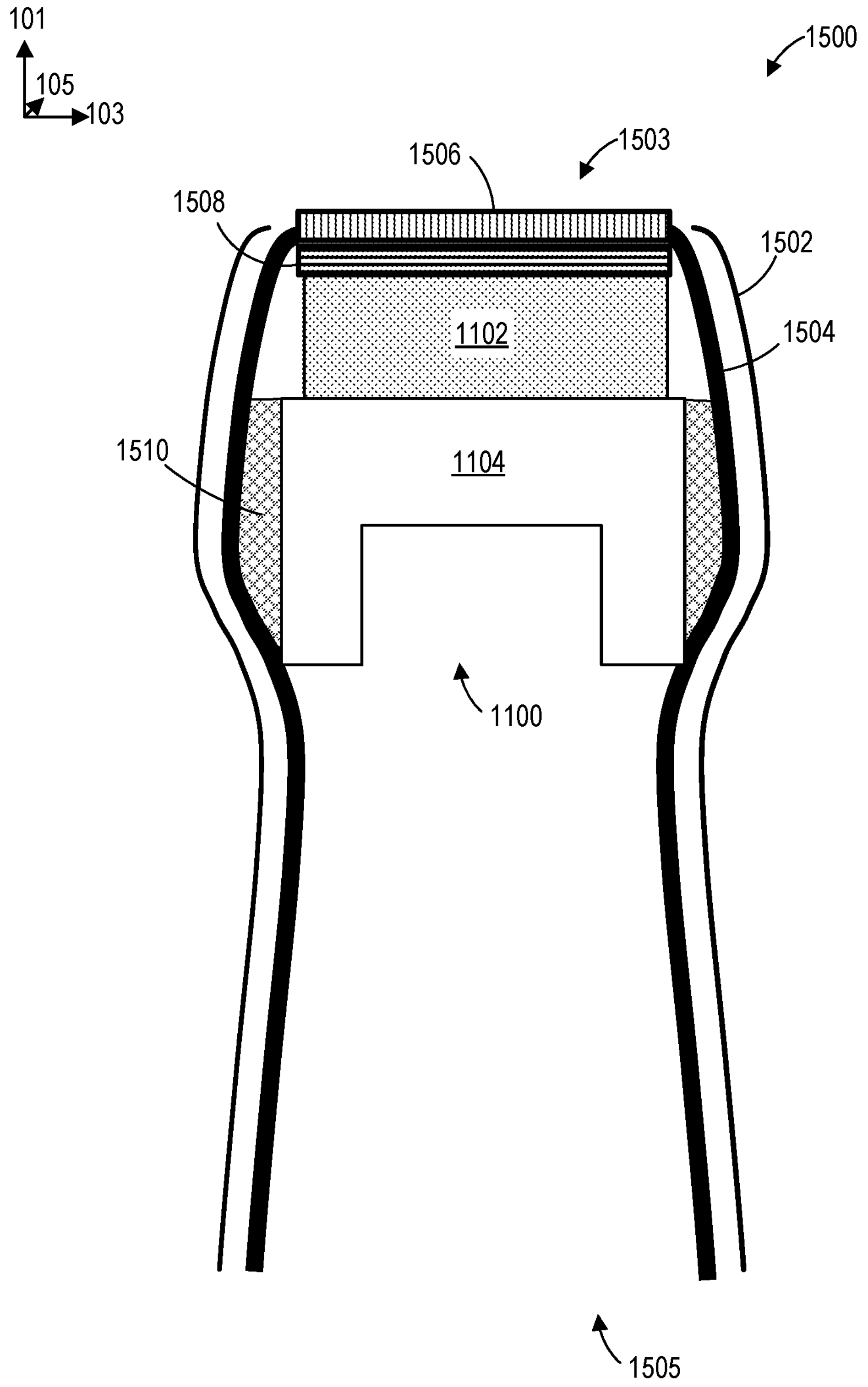
FIG. 15 shows a first transducer probe incorporating the modified backing of FIGS. 11, according to an embodiment.
Figure 16:
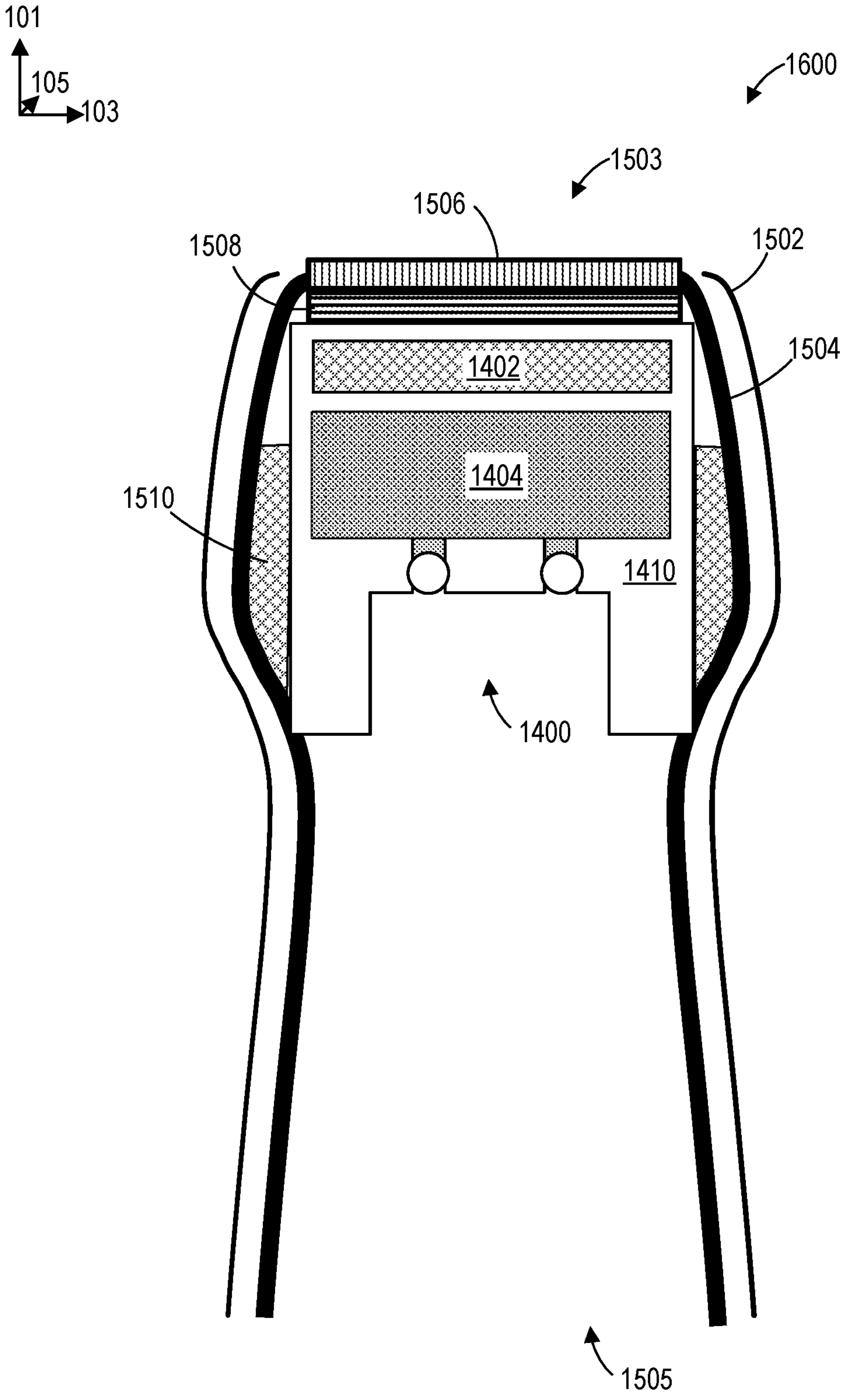
FIG. 16 shows a second transducer probed incorporating the modified backing of FIG. 14, according to an embodiment.

The following description relates to various embodiments of a backing for a transducer probe. The backing may attenuate acoustic energy scattered in directions other than a direction of signal propagation from the transducer probe, thereby improving image quality by reducing noise and ring-down time. As shown in FIG. 1, a backing may be included in an acoustic stack of a transducer probe, positioned behind a piezoelectric material of the acoustic stack. In one example, the backing may be a modified backing that is additively manufactured to have high thermal conductivity in addition to high acoustic attenuation. The modified backing may be fabricated with a structure that attenuates acoustic energy via scattering and absorption, as illustrated in FIG. 2. Numerous variations in a configuration of the modified backing may be possible when the modified backing is additively manufactured, the variations allowing acoustic and thermal properties of the modified backing to be moderated. For example, the modified backing may have a curved geometry, as shown in FIG. 3, may be at least partially enclosed by an external wall, as shown in FIG. 4, or may include internal structures, as shown in FIGS. 5-7. As depicted in FIG. 8, the modified backing may also have a gradient structure. A porous matrix of the modified backing may be at least partially filled with a filler and sealed, as shown in FIGS. 9 and 10, respectively. It will be appreciated that the examples of fillers described with respect to FIGS. 9 and 10 may be used for any of the modified backings shown and described herein. In some instances, the modified backing may include an integrated heat sink, examples of which are depicted in FIGS. 11-14. By additively manufacturing the modified backing, the modified backing may be readily incorporated into a transducer probe, as illustrated in FIGS. 15 and 16. An example of method for fabricating a modified backing is elaborated in FIG. 17.

Before further discussion of the approach for manufacturing a modified backing with high acoustic attenuation and high thermal conductivity, a general overview of an acoustic stack for a transducer probe is illustrated in FIG. 1 and described below. In one example, the transducer probe may be an ultrasound probe, although other types of probes demanding absorption of stray acoustic energy and thermal management have been considered.

An ultrasound probe includes one or more active components for generating an ultrasonic signal. An example of an active component, or piezoelectric element 102 of an ultrasound probe is shown in a schematic diagram of an acoustic stack 100 in FIG. 1, with a central axis 104. A set of reference axes are provided, indicating a propagation (e.g., signal propagation) direction 101, an azimuth direction 103, and an elevation direction 105. In other examples, the set of reference axes may represent a z-axis 101, an x-axis 103, and a y-axis 105. The piezoelectric element 102 is shown in FIG. 1 with the central axis 104 parallel with the propagation direction 101.

It will be noted that while the acoustic stack 100 is shown with a propagation direction described as parallel with the z-axis in FIG. 1, other examples may include a propagation direction that is angled relative to the z-axis, depending on a shape of a piezoelectric element array. For example, the ultrasound probe may be curvilinear or phased array, thus generating non-linear beams that are not parallel with the z-axis. Furthermore, while the examples shown and described herein are directed to ultrasound applications, the methods and systems described below may be applicable to a variety of sensor array types.

While a single piezoelectric element is shown in FIG. 1, the ultrasound probe may include a plurality of piezoelectric elements arranged in an array and individually coupled to an electrical energy source by wires. Each electrical circuit formed of one or more piezoelectric elements may be a transducer. In some examples, the transducer may include an array of piezoelectric elements which may arranged in a variety of patterns, or matrices, including one-dimensional (1D) linear, two-dimensional (2D) square, 2D annular, etc. Each transducer may be electrically insulated from adjacent transducers but may all be coupled to common layers positioned above and below the piezoelectric element, with respect to the propagation direction. The plurality of piezoelectric elements and accompanying layers may be enclosed by an outer housing of the ultrasound probe which may be, for example, a plastic case with a variety of geometries. For example, the outer housing may be a rectangular block, a cylinder, or a shape configured to fit into a user's hand comfortably. As such, components shown in FIG. 1 may be adapted to have geometries and dimensions suitable to fit within the outer housing of the ultrasound probe.

The piezoelectric element 102 may be a block formed of a material, such as lead zirconate titanate, that deforms and vibrates when a voltage is applied by, for example, a transmitter. In some examples, the piezoelectric element 102 may be a single crystal with crystallographic axes, such as PMN-PT (Pb $(Mg_{1/3}Nb_{2/3})O_3$—$PbTiO_3$). The vibration of the piezoelectric element 102 generates an ultrasonic signal formed of ultrasonic waves that are transmitted out of the ultrasound probe in a direction indicated by arrows 107, e.g., along the propagation direction 101. The piezoelectric element 102 may also receive ultrasonic waves, such as ultrasonic waves reflected from a target object, and convert the ultrasonic waves to a voltage. The voltage may be transmitted to a receiver of the ultrasound imaging system and processed into an image.

Electrodes 114 may be in direct contact with the piezoelectric element 102 to transmit the voltage via wires 115, the voltage converted from ultrasonic waves. The wires 115 may be connected to a circuit board (not shown) to which a plurality of wires from electrodes of the plurality of piezoelectric elements may be fixed. The circuit board may be coupled to a coaxial cable providing electronic communication between the ultrasound probe and the receiver. In one example, the circuit board may be one or more ASICs electrically coupled to the piezoelectric element 102 by an electrical interfacing structure. Together the electrodes 114, the wires 115, and the circuit board may form an electrical circuit or electrical actuator of the piezoelectric element 102. In some examples, the electrical circuit may be a flex circuit, as an alternative to the one or more ASICs.

An acoustic matching layer 120 may be arranged above the piezoelectric element 102, with respect to the propagation direction 101, oriented perpendicular to the central axis 104. The acoustic matching layer 120 may be a material positioned between the piezoelectric element 102 and a target object to be imaged. By arranging the acoustic matching layer 120 in between, the ultrasonic waves may first pass through the acoustic matching layer 120, and emerge from the acoustic matching layer 120 in phase, thereby reducing a likelihood of reflection at the target object. The acoustic matching layer 120 may shorten a pulse length of the ultrasonic signal, which may increase an axial resolution of the signal. Further, in some examples, multiple (e.g., more than one) acoustic matching layer may be included in the acoustic stack 100.

A backing layer 126 may be arranged below the piezoelectric element 102, with respect to the propagation direction 101. In some examples, the backing layer 126 may be a block of material that extends along the azimuth direction 103 (and the elevation direction 105) so that each of the plurality of piezoelectric elements in the ultrasound probe are directly above the backing layer 126, with respect to the propagation direction 101. The backing layer 126 may be configured to absorb ultrasonic waves directed from the piezoelectric element 102 in a direction opposite of the direction indicated by arrows 107. Further, the backing layer 126 may attenuate any stray ultrasonic waves deflected by the transducer and probe in directions other than directions useful for imaging, e.g., directions outside of a range of signal angles that may be transmitted and received by the ultrasound probe based on its specific size and frequency range. A bandwidth of the ultrasonic signal, as well as the axial resolution, may be increased by the backing layer 126.

In one example, as described herein, the backing layer 126 may be a modified backing that is fabricated via additive manufacturing. Additive manufacturing of the modified backing may introduce flexibility into its configuration, including a geometry of the modified backing, a porosity, incorporation of internal structures or inclusions, and integration of the modified backing with other components. Furthermore, by controlling such aspects of the modified backing, the modified backing may have thermal management capabilities. For example, the modified backing may be configured to be thermally conductive, or be fabricated with a thermally conductive structure, such as a heat sink, as a single unit. Further details of the modified backing are provided below, with reference to FIGS. 2-17.

In some examples, the backing layer 126 may be positioned under (e.g., with respect to the z-axis 101) at least one ASIC of the ultrasound probe. In such examples, the backing layer 126 may be formed from a continuous, e.g., undiced, material. Dicing of the backing layer 126 may be challenging due to a thickness of the backing layer 126, which may be greater than other layers of the acoustic stack 100. In other examples, the acoustic stack 100 may also include a dematching layer (not shown in FIG. 1) arranged directly below the piezoelectric element 102 and between the piezoelectric element 102 and the backing layer 126. The dematching layer may be a high acoustic impedance layer that reflects a majority of the ultrasonic signal received by the ultrasound probe out of a front of the ultrasound probe (e.g., along the propagation direction 101), allowing a reflected portion of the ultrasonic signal to be used for imaging.

As described above, a modified backing may be included in an acoustic stack in place of a conventional backing layer. The modified backing may be additively manufactured, and therefore customizable according to a target application while incurring costs during production that are lower than costs of conventional transducer probes. As an example, the modified backing may have a porous matrix that enable random or pseudo-random scattering of acoustic energy and absorption of the scattered acoustic energy. A material and structure of the porous matrix may be nonhomogeneous, which is enabled via additive manufacturing. Further, by forming the modified backing by additive manufacturing, other probe components may be integrated into the modified backing, reducing a number of individual parts of the probe, and increasing an effectiveness of the parts. For example, the modified backing may include at least one structural element, including pore configuration, fillers, and heat conducting structures, that allow the modified backing to provide one or more of a target acoustic attenuation and a target thermal conductivity.

Scattering and absorption, e.g., attenuation, of acoustic energy reflected from a piezoelectric material in an acoustic stack is illustrated in FIG. 2. An example of a modified backing 200 is depicted in FIG. 2, the modified backing 200 being a porous matrix formed of one or more of aluminum, aluminum nitride, copper, titanium, tungsten, a metal alloy, and stainless steel, and including a filler material filling the porous matrix. A porosity and structure of the modified backing 200 may be random or pseudo-random such that the porosity, and corresponding structure (e.g. crystal structure or molecular structure), may be variable within the modified backing 200, or may be relatively uniform, while maintaining an ability to scatter the acoustic energy in different directions.

As shown in FIG. 2, incident acoustic energy, e.g., acoustic waves, may enter the modified backing 200 as indicated by arrows 202, in a direction opposite of the propagation direction 101. For example, the incident acoustic energy may be reflected into the modified backing 200 from a piezoelectric material arranged in front of the modified backing 200 relative to the propagation direction 101, as depicted in FIG. 1. The incident acoustic energy may have a first intensity upon entering the modified backing 200, as indicated by arrows 204.

The acoustic energy may then interact with the modified backing 200 and be redirected to travel in a different direction. For example, the acoustic energy may be reflected off of the structure of the matrix, such as at a pore. Further, vibration of the material of the modified backing 200 may be induced by the incident acoustic energy and may interfere destructively with the acoustic energy travelling therethrough. The intensity of the acoustic energy may decrease as it is scattered and absorbed by the porous matrix and filler, as indicated by arrows 206.

The acoustic energy may continue to be scattered and decreased in intensity through the modified backing 200 until the acoustic energy is fully dissipated. A number of reflections of the acoustic energy within the modified backing 200 that is demanded for complete absorption of the acoustic energy may vary, as shown in FIG. 2. The acoustic energy may be bounced in a variable manner within the modified backing 200 and dampened concurrently, thereby minimizing escape of the acoustic energy out from the modified backing 200.

Attenuative properties of the modified backing may be optimized by adjustment of various parameters of the modified backing, which may be enabled via additive manufacturing of the modified backing layer. For example, the modified backing may be formed having a near-net shape, thereby minimizing application of finishing processes, such as machining or grinding, to achieve a final, desired geometry of the backing layer. When formed with the near-net shape, the modified backing may be produced with a geometry that is very close to a desired final, or net shape of the modified backing. In some instances, additive manufacturing of the modified backing allows machining or grinding of the modified backing to be precluded. As one example, a shape of the modified backing may be selected, e.g., by an operator, during fabrication of the modified backing such that the modified backing is additively manufactured with a desired geometry. As an example, the modified backing may be fabricated for use in a curved probe, as shown in FIG. 3.

An example of a modified backing 300 having a curved geometry is depicted in FIG. 3. The modified backing 300 may have a matrix 302 composed of any of the materials provided above, and may be additively manufactured to have a specific shape. For example, the modified backing 300 may have a curved upper or front surface 304 to accommodate coupling to a curvilinear piezoelectric material used for, as one example, transabdominal imaging.

A bottom, or rear surface 306 of the modified backing 300 may have structural details to enable mechanical coupling of the modified backing 300 to adjacent components. For example, the rear surface 306 may include alignment elements 308, which may be slots configured to receive protrusions of components to be coupled to the rear surface 306 of the modified backing 300. The rear surface 306 may also include at least one recess 310 for receiving an electrical component 312.

The geometry of the modified backing may therefore be readily customized during manufacturing according to a target application. The modified backing shape may affect its ability to attenuate acoustic energy for a particular transducer shape, where the transducer shape may be application-specific. For example, curved transducers may allow acoustic waves to penetrate deeper into region of interest, providing in-depth imaging, while linear transducers enable high-resolution imaging at shallower depths. By forming the modified backing via a process that allows formation of near-net shape products, the modified backing may be fabricated with a geometry and detailed structural features with minimal additional processing and labor, which may broaden use of a particular modified backing matrix type for different probe applications.

Acoustic attenuation capabilities of an additively manufactured modified backing may also be varied according to a porosity of the modified backing. The porosity may be controlled during fabrication, e.g., printing, of the modified backing based on a selected (e.g., by an operator) pore size, pore structure (e.g., shape), and pore density or total porosity, according to a target application. For example, by decreasing pore size, the modified backing may attenuate acoustic energy at higher frequencies. A shape of the pores and total porosity of the modified backing may also affect how a material of the modified backing layer interacts with incident acoustic energy.

Additionally, by modifying manufacturing parameters during printing of the modified backing, the material of the modified backing may be formed with a target structure, such as a desired density orientation, alignment, etc. For example, a laser pass power, speed, direction, angle, hatching, print orientation, etc., may be adjusted to obtain desired structural properties in the modified backing, such as a target pore uniformity, pore size, pore shape, pore density, etc. By obtaining the desired structural properties, the modified backing may demonstrate target acoustic and thermal characteristics.

The modified backing may further be additively manufactured to provide thermal management properties. For example, heat may be transferred via thermal management structures of the modified backing from a front of the transducer probe to a rear of the transducer probe, away from a surface of the transducer probe that contacts a patient. By enabling the modified backing to conduct heat in a desired manner, operation of the transducer probe at a desired power level may be prolonged. In one example, as shown in FIG. 4, a modified backing 400 may be fabricated with one or more structures along an external surface of the modified backing 400, such as a solid external wall 402 surrounding a matrix 404 of the modified backing 400 and continuously coupled to the matrix 404. The external wall 402 may be formed of a same or different material as the matrix 404 but may have a higher density and lower porosity than the matrix 404. For example, the external wall 402 may include one or more of aluminum, aluminum nitride, copper, titanium, tungsten, metal alloys, and stainless steel, e.g., thermally conductive materials, and may be configured to have higher heat conductivity than the matrix 404.

The external wall 402 may at least partially enclose the matrix 404 and may not be detached from the matrix 404. As an example, the external wall 402 may extend across an upper or front surface 406 of the matrix 404, relative to the signal propagation direction 101, as well as side surfaces 408 of the matrix 404. By arranging the external wall 402 at least across the front surface 406 of the matrix 404, the external wall 402 may be positioned between a piezoelectric material of an acoustic stack and the matrix 404. The external wall 402 may direct heat away from an electric circuit (e.g., electrical actuator) of the piezoelectric material and around the matrix 404 to a rear side of the modified backing 400, as indicated by arrows 410, thereby transferring heat to other regions of a transducer that are distal to a patient and do not contact the patient. While the external wall 402 is depicted surrounding the front surface 406 and the side surfaces 408 of matrix 404, in other examples, the external wall 402 may have a different geometry.

For example, the external wall may not extend along all of the side surfaces of the matrix 404 or may not extend across the side surface at all. In such instances the external wall may be in contact with a heat absorbing component, such as a heat sink. Additionally, the external wall may be coupled to heat conducting structures embedded in the matrix of the modified backing, as shown in FIG. 5.

In FIG. 5, a modified backing 500 may include a first example of internal inclusions embedded therein. The internal inclusions may be heat conducting structures 502 extending through a matrix 504 of the modified backing 500 and may be formed of a same material as an external wall 506 of the modified backing 500. However, in other examples, the heat conducting structures 502 may be formed of a different thermally conductive material than the external wall 506.

The heat conducting structures 502 may form an internal lattice within the matrix 504 that provides a path of increased heat conduction through the matrix 504, as indicated by arrows 503. Each of the heat conducting structures 502 may be a discrete structure with segments such as branches 502*a* extending from a backbone 502*b* of each of the heat conducting structures 502. The backbone 502*b* of the heat conducting structures 502 may extend continuously from a front surface 508 of the matrix 504 to a rear surface 510 of the matrix 504, at an angle θ relative to the propagation direction 101. For example, the angle may be 0 degrees up to 80 degrees relative to the propagation direction 101.

The heat conducting structures 502 may be spaced apart from one another as shown in FIG. 5, or, in other examples, the heat conducting structures 502 may be interconnected to form a continuous lattice through the matrix 504. Furthermore, the modified backing 500 may have a variable quantities of the heat conducting structures 502, with each of the heat conducting structures 502 having variable quantities of branches 502*a*. The heat conducting structures 502 may be formed of a common material or may be formed of different materials within a given modified backing.

The heat conducting structures 502 may also affect attenuation of acoustic energy, in addition to heat management within the acoustic stack. For example, the heat conducting structures 502 may reflect acoustic energy scattered into the modified backing 500 from the piezoelectric material of the acoustic stack. By providing additional surfaces for reflecting the acoustic energy, an overall path length that the acoustic energy travels within the modified backing 500 may increase, which increases attenuation of the acoustic energy. Attenuative properties of the modified backing 500 provided by the heat conducting structures 502 may be modified by varying physical parameters of the heat conducting structures 502, such as material and a texture thereof, quantity (e.g., density) of the heat conducting structures, distribution and orientation in the matrix 504, number of branches, dimensions of the heat conducting structures, etc.

A modified backing 600 with a second example of internal structures embedded therein is depicted in FIG. 6. The internal structures, or heat conducting structures 602, of the modified backing 600 may be embedded within a matrix 604 of the modified backing 600 and may extend from a front surface 606 of the matrix 604 to a rear surface 608 of the matrix 604. As described above, the heat conducting structures 602 may be formed of a thermally conductive material that may be of a same or different type as an external wall 610 of the modified backing 600.

The heat conducting structures 602 may be discrete units spaced apart from one another and having segments that form shapes resembling zig-zags or lightning bolts. In other examples, however, the heat conducting structures 602 may be interconnected and may also vary with respect to angles and orientation. Further, the heat conducting structures 602 may be composed of a common material or of different materials.

Similar to the heat conducting structures 502 of FIG. 5, the heat conducting structures 602 of FIG. 6 may provide thermally conductive paths through the matrix 604 of the modified backing 600 while the external wall 610 may direct heat around the matrix 604. A combined effect of the external wall and the heat conducting structures of FIGS. 5 and 6 may efficiently transfer heat away from an electric circuit coupled to a piezoelectric material of an acoustic stack, the electric circuit adjacent to the modified backing 600. In addition, as described above, the heat conducting structures 602 may also moderate attenuation of acoustic energy by the modified backing 600. An effect of the heat conducting structures 602 on attenuation may be similarly dependent on an orientation, quantity, material, dimensions, spacing, etc., of the heat conducting structures 602.

A modified backing 700 with a third example of internal structures embedded therein is depicted in FIG. 7. The internal structures, or heat conducting structures 702, of the modified backing 700 may be embedded within a matrix 704 of the modified backing 700 and may extend from a front surface 706 of the matrix 604 to a rear surface 708 of the matrix 704. As described above, the heat conducting structures 702 may be formed of a thermally conductive material that may be of a same or different type as an external wall 710 of the modified backing 700.

In comparison to the heat conducting structures of FIGS. 5 and 6, the heat conducting structures 702 of FIG. 7 may have a simple and planar geometry, extending linearly through the matrix 704 without any turns, bends, branches, etc. For example, the heat conducting structures 702 may be similar to the backbone 502*b* of each of the heat conducting structures 502 of FIG. 5. The heat conducting structures 702 may provide fewer surfaces than the heat conducting structures of FIGS. 5 and 6, for example, to reflect acoustic energy scattered into the modified backing from a piezoelectric material coupled thereto. Reflection and scattering provided by the heat conducting structures 702, however, may instead be varied based on an angle ¢ of the heat conducting structures 702 relative to the propagation direction 101.

A capacity of a modified backing for attenuating acoustic energy while conducting heat efficiently across the modified backing may be adjusted based on a geometry of heat conducting structures embedded in its matrix. By varying an amount of segments of the heat conducting structures, interaction of the heat conducting structures with acoustic energy may be modified. By forming the heat conducting structures of a more thermally conductive material than a matrix of the modified backing, and configuring the heat conducting structures to extend from a side of the matrix proximate to a piezoelectric material, the heat conducting structures may provide a direct path for heat transfer through the modified backing to conduct heat away from the piezoelectric material and an electrical circuit generating the heat. The thermal conductivity and acoustic attenuation properties of the modified backing may be further moderated based on a density of the heat conducting structures, e.g., a quantity and spacing, within the matrix, and an orientation/angle of the heat conducting structures.

When fabricated via additive manufacturing, the modified backing may be formed having target thermal conductivity and acoustic attenuation characteristics. For example, the thermal conductivity of the modified backing, which may have thermal management structures such an external wall and/or internal heat conducting structures as illustrated in FIGS. 5-7, may be at least 20 Watts per meter Kelvin (W/m·K). In some examples, the thermal conductivity may be up to at least 40 W/m·K. The attenuation of acoustic energy provided by the modified backing may greater than 10 decibels per millimeter (dB/mm) at 3 MHz, for example.

In addition, or as an alternative, to external and/or internal heat conducting structures, a modified backing may have a gradient structure that moderates its acoustic and/or thermal properties. An example of a modified backing 800 having a gradient structure is illustrated in FIG. 8. The modified backing 800 may have a matrix 802 at least partially enclosed by an external wall 804. As described above, the external wall 804 may conduct heat around the matrix 802, away from an electrical circuit of a piezoelectric material.

The matrix 802 may be graded to have a property that varies along the propagation direction 101. As one example, matrix 802 may have a first zone 802*a* with a first porosity, a second zone 802*b* with a second porosity, and third zone 802*c* with a third porosity, the second zone 802*b* arranged between the first zone 802*a* and the third zone 802*c*. The first porosity may be lower than the second porosity, which may be lower than the third porosity. However, in other examples, the porosity gradient may be reversed or the porosity may not be sequentially graduated. Further, in other examples, a different parameter may be graduated along the propagation direction 101, instead of the porosity.

For example, a pore structure, a type of filler filling the pores, an amount of filler, a uniformity of the pores, a pore size, etc., may be varied in a controlled manner across the modified backing. The gradient structure of the matrix 802 may affect acoustic attenuation by incorporating zones that interact differently with acoustic energy. For example, the different porosities of the zones of the matrix 802 of FIG. 8 may provide regions with different surfaces that reflect acoustic energy as well as regions that vibrate at different frequencies when excited to destructively interfere with the acoustic energy. The gradient structure may also conduct heat differently along its zones. For example, regions with lower porosity or a first type of filler may conduct heat more efficiently than regions with higher porosity or a second type of filler that is different from the first type.

As discussed above, a filler may be added to a porous structure of a modified backing to enhance acoustic and/or thermal properties of the modified backing compared to an unmodified backing. In one example, the filler may be introduced to the matrix in a liquid state, allowing the filler to be injected into the matrix, as shown in FIGS. 9 and 10. A modified backing 900 is depicted in FIGS. 9 and 10 having a matrix 902 entirely enclosed within an external wall 904. The external wall 904 may be thermally conductive, as elaborated above, and the matrix 902 may be porous. For example, the matrix 902 may be a foamed structure, having randomly or uniformly distributed pores.

The external wall 904 may include ports 906, which may be fill and/or vent ports, as openings in the external wall 904 that fluidically couple the matrix 902 (e.g., fluid in the pores of the matrix, such as air) to fluid outside of the modified backing 900. Although two of the ports 906 are shown in FIG. 9, the external wall 904 may include any number of ports arranged at various locations around the matrix 902. By providing the ports 906 in the external wall 904, a filler 908 may be added to the matrix 902 after the modified backing 900 is additively manufactured. For example, the filler 908, which may be a fluid, may be injected through the ports 906 using an injector 910, as illustrated in FIG. 9. The external wall 904 may be an impermeable barrier around the matrix 902 that maintains the filler within the matrix 902 of the modified backing 900 during injection of the filler 908.

As another example, the filler may be added to the matrix 902 by a vacuum impregnation process. For example, a separate mold may be used to enclose the matrix 902 and the matrix 902 may be maintained at low pressure to draw the filler, in liquid form, into the matrix 902. The filler may be cured and the matrix 902 removed from the mold and machined to achieve a final, target shape. As such, the external wall 904 is not demanded to provide a solid barrier around the matrix 902 for containing the filler.

The filler 908 may fill at least a portion of the pores of the matrix 902, forming a filled region 912 and an unfilled region 914 of the matrix 902. In some examples, the pores of the matrix 902 may be entirely filled with the filler and the unfilled region 914 may not be present. In other examples, the matrix 902 may include more than one filled region 912, each of the filled regions including a different type of filler.

In one example, after the filler 908 is added to the matrix 902, the filler 908 may be allowed to cure with the ports 906 remaining open to vent any gases generated during curing. Alternatively, the ports 906 may be sealed when injection of the filler 908 is complete. As shown in FIG. 10, the ports 906 may be sealed with ball bearings 1000, thereby sealing the filler 908 within the modified backing 900 while the filler 908 remains in a liquid phase. Other types of sealing devices or structures are possible, however. Further, the seal devices or structures may be permanent or semi-permanent (e.g., removable).

The filler of the modified backing may be a material that modifies acoustic and/or thermal properties of the modified backing and may be selected during manufacturing to provide a target range of attenuation and/or thermal conductivity. By utilizing a material that is at least introduced to the modified backing as a fluid, the filler may be readily added to the modified backing. The filler may be, for example, one or more of epoxies, silicones, phase change materials, and scattering particles formed of phenolic micro-balloons, tungsten, metals or metal oxides, silicone, glass, etc.

As an example, acoustic attenuation of the modified backing may be increased by filling the matrix with a lossy epoxy. As another example, the matrix may be filled with a phase change material to increase thermal capacity. The phase change material may be a liquid-solid phase change material that transitions to a solid phase material when a temperature of the modified backing decreases to a threshold phase change temperature and returns to a liquid state when the temperature increases above the threshold phase change temperature, thereby absorbing and storing thermal energy. The phase change material may be selected to have a phase change temperature that corresponds to an operating temperature range of the modified backing. For example, the phase change material may have a phase change temperature of about 40° C., or in a range of 30° C. to 50° C. In one example, the phase change material may be paraffin wax. The paraffin wax may be initially heated to melt the paraffin wax, allowing it to be readily added to the matrix where the paraffin wax may cool and solidify. When exposed to heat during operation of the transducer probe, the paraffin wax may absorb heat and melt, storing heat energy as a liquid, which may be released after the transducer is no longer operating and cools down.

Figure 11:
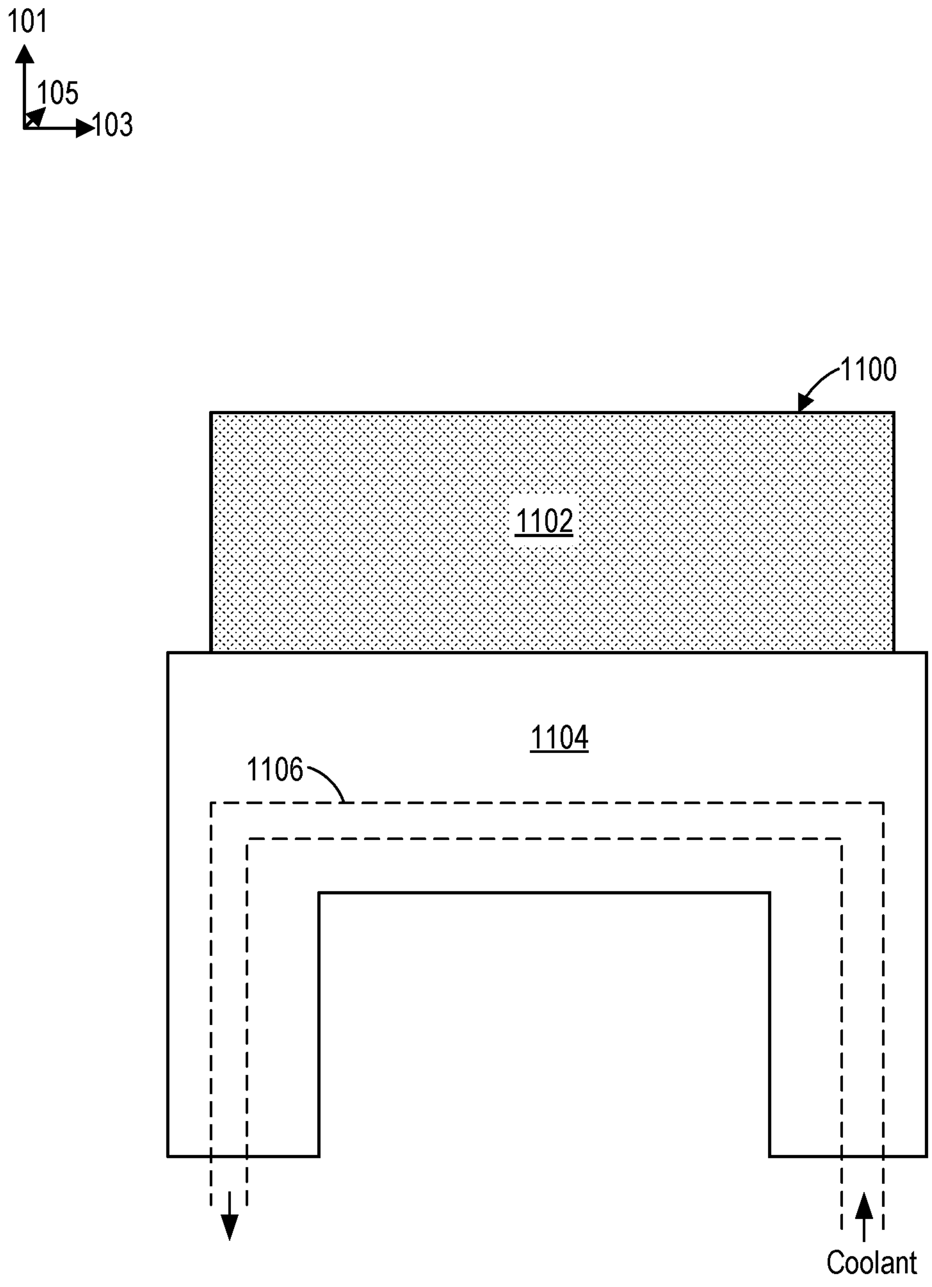
FIG. 11 shows a first example of a modified backing having an integrated heat sink, according to an embodiment.

In addition to controlling attenuation and thermal management of the modified backing, additively manufacturing the modified backing allows the modified backing to be integrated with, e.g., formed continuously as a single unit, support structures of a transducer probe. For example, one or more of the support structures may be fabricated to be continuous with and contiguous with a porous matrix of the modified backing. In other words, the one or more support structures and the porous matrix may be fixedly coupled to one another and not detachable. The support structures may include components that provide structural support and/or thermal management, such as a heat sink, where the heat sink may also be a thermal management structure that draws heat out of the porous matrix of the modified backing and transfers the heat to a rear of the transducer probe. An example of a modified backing 1100 having a matrix 1102 integrated with a heat sink 1104 is shown in FIG. 11. The heat sink 1104 may be fabricated with the matrix 1102 in a single process, to form the modified backing as a continuous unit, thereby precluding additional coupling mechanisms, such as adhesives. In other words, the heat sink 1104 may be continuously coupled to the matrix 1102, and more specifically, may be continuously coupled to a rear side of the matrix 1102.

The heat sink 1104 may be formed of a thermally conductive material, such as aluminum or copper, and may be fabricated with a geometry corresponding to available space within a transducer probe housing. In some examples, the modified backing 1100 may be manufactured with at least one internal cooling passage 1106 through which a coolant may flow. The internal cooling passage 1106 may allow the coolant to extract heat from the heat sink 1104, as depicted in FIG. 11, or may extend through both the heat sink 1104 and the matrix 1102 to draw heat out of both portions of the modified backing 1100. Additionally, in some examples, the matrix 1102 may include internal heat conducting structures, such as the heat conducting structures depicted in FIGS. 5-7.

Figure 12:
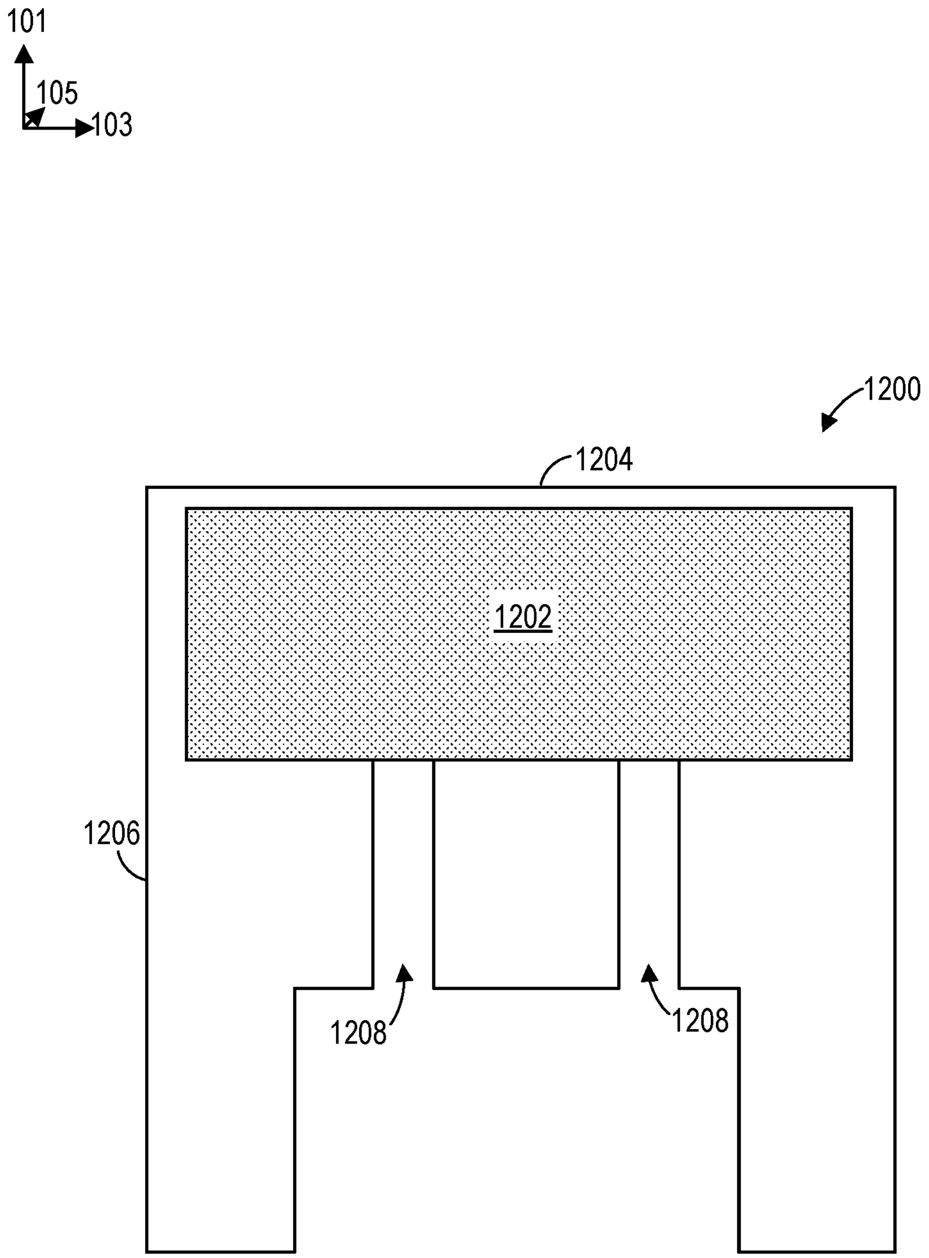
FIG. 12 shows a second example of a modified backing having an integrated heat sink, according to an embodiment.

Further, the geometry of the heat sink of the modified backing may be modified to also form an exterior wall around the matrix that is continuous with the heat sink. A filler may be added to the modified backing, as shown in FIG. 9. For example, as illustrated in FIG. 12, a modified backing 1200 may be a single, continuous unit that includes a matrix 1202, an external wall 1204, and a heat sink 1206. The external wall 1204 may be continuous with the heat sink 1206 such that the matrix 1202 is entirely enclosed by the external wall 1204 and the heat sink 1206. In one example, the external wall 1204 and the heat sink 1206 may be formed of a common material. The heat sink 1206 may include ports 1208 providing openings in the heat sink 1206 that allow the matrix 1202 to be filled with a filler.

Figure 13:
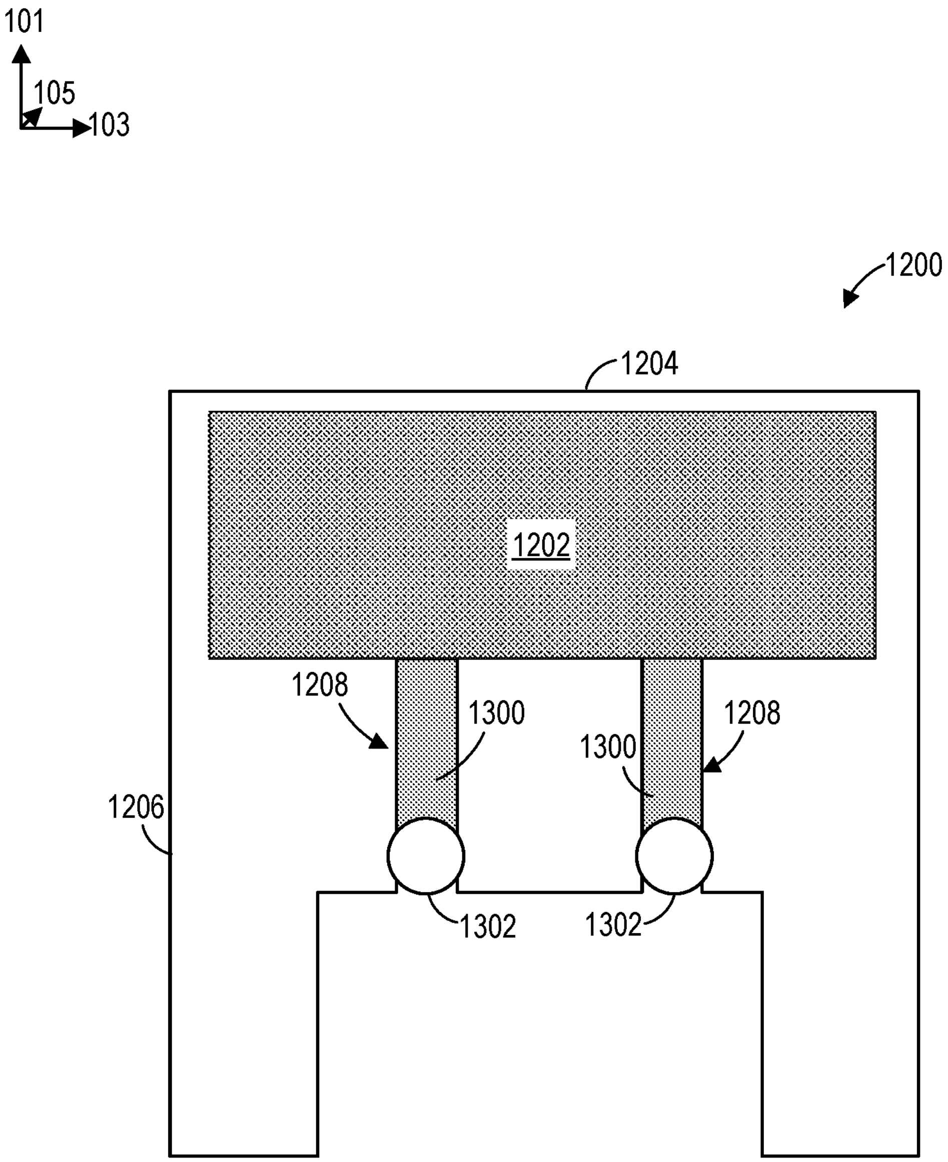
FIG. 13 shows the modified backing of FIG. 12 filled with a filler and sealed, according to an embodiment.

For example, the modified backing 1200 is shown in FIG. 13 with a filler 1300 filling pores of the matrix 1202 and the ports 1208. The filler 1300 may be injected using an injector, such as the injector 910 of FIG. 9, for example, through the ports 1208. As described above, a number of the ports 1208 depicted in FIG. 12 is exemplary and other examples may have other quantities of the ports. The ports 1208 may be plugged with seals 1302, such as ball bearings, which may seal the filler 1300 within the matrix 1202 and the ports 1208.

Figure 14:
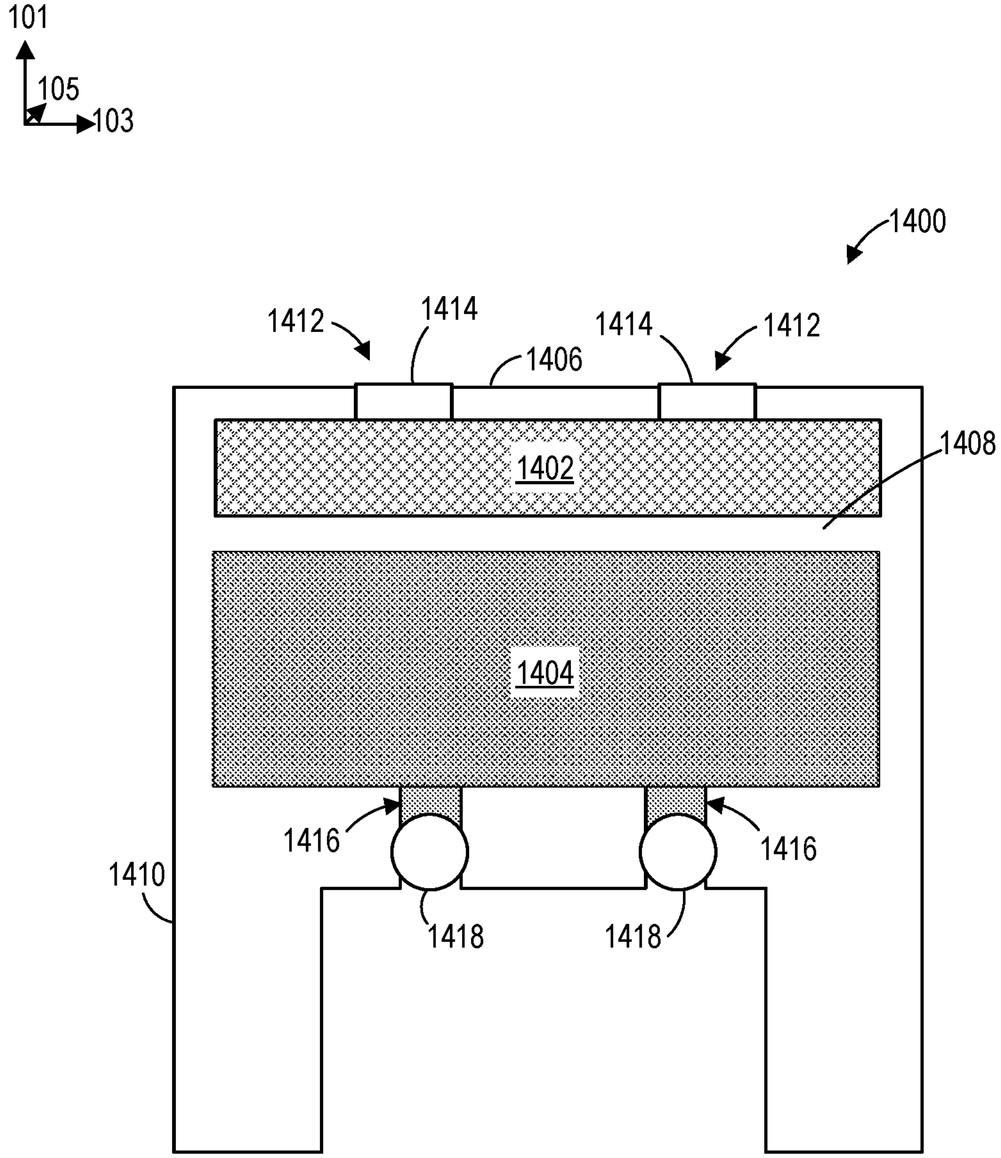
FIG. 14 shows a third example of a modified backing having an integrated heat sink, according to an embodiment.

Turning to FIG. 14, another example of a modified backing 1400 is shown having components that are integrated during additive manufacturing. The modified backing 1400 includes an attenuating region 1402, a heat storage region 1404, an external wall 1406, an internal wall 1408, and a heat sink 1410. The external wall 1406 may extend across a front surface of the attenuating region 1402 and side surfaces of the heat storage region 1404. The attenuating region 1402 may be separated from the heat storage region 1404 by the internal wall 1408, which may be continuous with the external wall 1406, which may, in turn be continuous with the heat sink 1410. In one example, the external wall 1406, the internal wall 1408, and the heat sink 1410 may be formed of a common material. Additionally, in some examples, the attenuating region 1402 and/or the heat storage region 1404 may include internal, heat conducting structures, such as the heat conducting structures depicted in FIGS. 5-7

The attenuating region 1402 may be positioned closer to a piezoelectric material of an acoustic stack than the heat storage region 1404 and may be a matrix having high attenuative properties, e.g., higher than the heat storage region 1404. For example, the matrix may be formed of any of the materials described previously and may be filled with a lossy epoxy. The lossy epoxy may be injected into the matrix of the attenuating region 1402 through a first set of ports 1412 forming openings in the external wall 1406. The first set of ports 1412 may be sealed closed with seals 1414. For example, the seals 1414 may be plugs.

The heat storage region 1404 may include a matrix having high thermal absorption, e.g., higher than the attenuating region 1402. For example, the matrix may be formed of any of the materials described previously and may be filled with a phase change material. The phase change material may absorb and store heat as it undergoes phase transitions. The matrix of the heat storage region 1404 may be filled with the phase change material via a second set of ports 1416 forming openings in the heat sink 1410. The second set of ports 1416 may be sealed by seals 1418. The seals 1418 may be, for example, ball bearings.

In the examples of FIGS. 11-14, the modified backing may be fabricated with integrated components, e.g., the external wall, the matrix, and the heat sink, which provide thermal and acoustic management of the modified backing. By manufacturing the components concurrently, as a continuous unit, parts of a transducer probe may be consolidated, leading to reduced costs compared to conventional manufacturing processes where the parts are manufactured individually and demand subsequent assembly. As well, a number of thermal interfaces included in the transducer probe may be decreased, which may increase a performance of the probe.

Further, the additive manufacturing of the modified backing with integrated components enables a geometry of the modified backing to be customized to have specific dimensions and shapes with minimal processing. For example, the modified backing 1100 of FIG. 11 and the modified backing 1400 of FIG. 14 are shown incorporated into a first transducer probe 1500 and a second transducer probe 1600 in FIGS. 15 and 16, respectively.

The first and second transducer probes both have a probe housing 1502, a heat spreader 1504, a lens 1506, a piezoelectric material 1508, and thermal interface material (TIM) 1510. The piezoelectric material 1508 may be above the modified backing of each transducer probe, with respect to the propagation direction 101. Various other probe components may be included in the probes, such as electrical devices, circuits, connectors, etc., but are omitted in FIGS. 15 and 16 for clarity. The probe housing 1502 may enclose all inner components of the respective probe except for the lens 1506 and may have a geometry that corresponds to its specific application. For example, the probe housing 1502 may be shaped for a phased or sector transducer array as shown in FIGS. 15 and 16, or for a convex transducer array or a linear transducer array.

The heat spreader 1504 may be a thin, continuous layer of a metal, such as aluminum, or other heat conductive material, extending along an inner surface of the probe housing 1502 across the entire probe housing. The heat spreader 1504 may transfer heat from a front end 1503 of the respective probe to a rear end 1505 of the probe, thereby contributing to thermal management of the probe. The TIM 1510 may be a compliant material, such as clay or silicone, used to fill in spaces between the heat spreader 1504 and the modified backing 1100 or 1400 and provide conduction of heat from the heat sink 1104 and 1410 to the heat spreader 1504.

As shown in FIG. 15, the modified backing 1100 may be sized to fit into an available packaging space behind the piezoelectric material 1508. For example, dimensions of the matrix 1102 and of the heat sink 1104 may be selected during additive manufacturing of the modified backing 1100 to fit within an inner volume of the probe housing 1502. Further, a shape of the modified backing 1200 may be selected, e.g., by an operator or a computing system, such that a size of the heat sink 1104 may be maximized within the available packaging space.

As shown in FIG. 16, the modified backing 1400 of FIG. 14 may instead be arranged within the available packaging space of the probe housing 1502, behind the piezoelectric material 1508. For example, the modified backing 1400 may be fabricated with a similar footprint as the modified backing 1100 of FIGS. 11 and 15. Additive manufacturing of the modified backing therefore allows flexibility in a configuration of the modified backing to optimize both a performance of the modified backing and its geometry for positioning behind the piezoelectric material, according to a particular probe. Additionally, additive manufacturing enables details of the modified backing to be tuned according to usage to a higher level of optimization than can be achieved by conventional manufacturing processes. For example, the probes depicted in FIGS. 15 and 16 may be configured with any of the examples of the modified backing shown in FIGS. 3-14, as well as other configurations not described herein, without adding complexity or cost to the manufacturing process.

When adapted with a modified backing, a probe may thereby be configured with different domains. For example, the second transducer probe 1600 may include an attenuating domain (e.g., the attenuating region 1402), a heat storage domain (e.g., the heat storage region 1404), and a solid heat sink domain (e.g., the heat sink 1410). Each domain may provide a specific operational task and may each be incorporated into a single structure that can be manufactured as a single multi-domain, near-net shape component.

Figure 17:
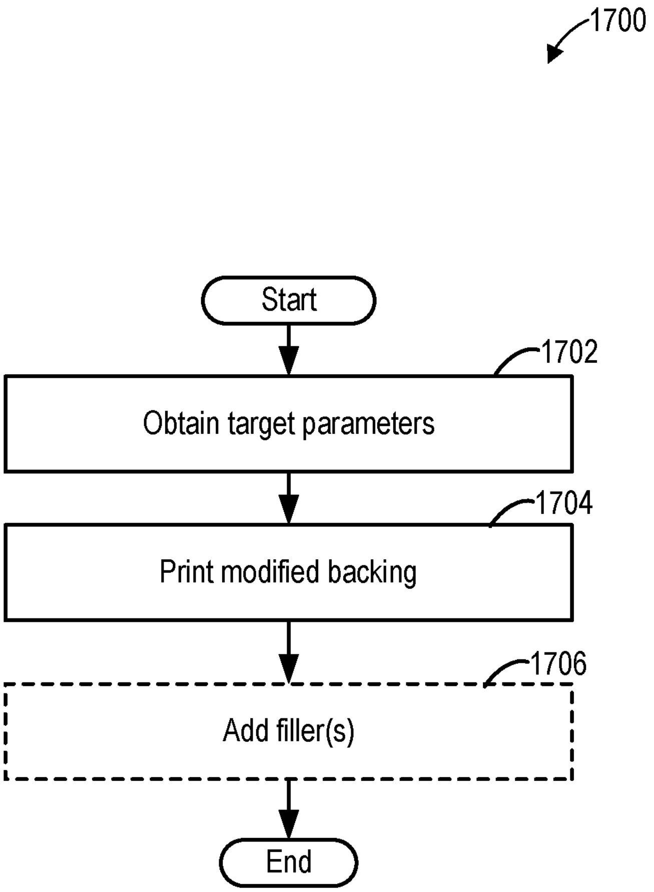
FIG. 17 shows a method for fabricating a modified backing, according to an embodiment.

An example of a method 1700 for manufacturing a modified backing for a transducer probe is shown in FIG. 17. The method may be executed by an additive manufacturing system, such as a 3D printer, configured to receive input from an operator and having executable instructions stored on a memory of a controller of the additive manufacturing system. The modified backing may be any of the examples of modified backings depicted in FIGS. 3-14.

At 1702, the method includes obtaining target parameters for the modified backing. The target parameters may be stored at the memory of the controller, retrieved from a database accessible by the controller, and/or input to the controller by the operator. For example, the target parameters may include a type of probe in which the modified backing is to be incorporated, a target acoustic attenuation, a target thermal conductivity, and one or more materials from which the modified backing is to be formed. The target parameters may further include a porosity, pore structure, and distribution of pores of a matrix of the modified backing, variations in the pores to form a gradient structure in the matrix, a quantity, geometry, and orientation of internal heat conductors, an arrangement of an external wall around the matrix, a presence of ports in the external wall, a presence of an internal wall arranged between two matrices, a shape of a heat sink to be integrated with the matrix, etc. In addition, the target parameters may include manufacturing conditions, such as print parameters, including laser power, printing speed, print directions, print angle, print hatching print orientation, etc.

At 1704, the method includes printing the modified backing according to the target parameters. Optionally, at 1706, at least one filler may be added to the matrix or matrices of the modified backing. For example, the filler may be a fluid that may be injected into the matrix through the ports of the external wall or ports in the heat sink. Alternatively, the filler may be incorporated into the additive backing matrix with a vacuum impregnation process utilizing a separate mold. In examples where the modified backing has more than one matrix, e.g., as shown in FIGS. 14 and 16, different fillers may be injected into the matrices. Additionally or alternatively, more than one type of filler may be injected into a single matrix. The filler may be, for example, a material that modifies acoustic and/or thermal properties of the modified backing and may remain a fluid after injection or may be cured to become a non-liquid, such as a solid. In one example, the filler may be a phase change material that may be injected as a fluid and may undergo a phase transition to a solid when exposed to temperatures below a phase transition temperature. In examples, where the filler is not cured, the ports in the external wall and/or heat sink may be plugged and sealed to inhibit loss of the filler through the ports.

In this way, a backing for a transducer probe may be provided. The embodiments of the backing described herein may further be applied to industrial, non-destructive probes used for detecting structural deficiencies, for example. The backing may be a modified backing having acoustic and/or thermal management capabilities. Acoustic and/or thermal properties of the modified backing may be readily incorporated into the modified backing during fabrication of the modified backing via additive manufacturing. The additively manufactured modified backing may include various elements to optimize its ability to attenuate acoustic energy and conduct heat away from a piezoelectric material of the transducer. For example, the various elements may include a porous matrix to which a filler may be added, an external wall to direct heat around the matrix, internal heat conducting structures embedded in the matrix, and a heat sink, where the elements may be manufactured together as a single integrated unit. Properties and a geometry of the modified backing may be readily varied based on adjustment to printing parameters to optimize the modified backing for a particular application or probe. As a result, the modified backing may be manufactured at low cost and with a high degree of flexibility, which may increase a performance of the transducer probe.

A technical effect of additively manufacturing a modified backing for a transducer probe is that acoustic attenuation and thermal management provided by the modified backing may be increased and/or modified according to a target usage.

FIGS. 1-16 show example configurations with relative positioning of the various components. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space therebetween and no other components may be referred to as such, in at least one example. As yet another example, elements shown above/below one another, at opposite sides to one another, or to the left/right of one another may be referred to as such, relative to one another. Further, as shown in the figures, a topmost element or point of element may be referred to as a "top" of the component and a bottommost element or point of the element may be referred to as a "bottom" of the component, in at least one example. As used herein, top/bottom, upper/lower, above/below, may be relative to a vertical axis of the figures and used to describe positioning of elements of the figures relative to one another. As such, elements shown above other elements are positioned vertically above the other elements, in one example. As yet another example, shapes of the elements depicted within the figures may be referred to as having those shapes (e.g., such as being circular, straight, planar, curved, rounded, chamfered, angled, or the like). Further, elements shown intersecting one another may be referred to as intersecting elements or intersecting one another, in at least one example. Further still, an element shown within another element or shown outside of another element may be referred as such, in one example.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

The disclosure also provides support for a probe, comprising: an additively manufactured backing having a porous matrix, the porous matrix at least partially filled with at least one filler, and one or more thermal management structures, wherein the additively manufactured backing attenuates acoustic energy and enables a transfer of heat from a front of the probe to a rear of the probe. In a first example of the system, the porous matrix has a nonhomogeneous structure, and wherein a uniformity, size, shape, and spacing of pores of the porous matrix is modified by varying one or more of a laser pass power, a print speed, a print direction, a print angle, a print hatching, and a print orientation during fabrication of the porous matrix. In a second example of the system, optionally including the first example, the at least one filler includes one or more of a lossy epoxy, a silicone, scattering particles, and a phase change material, and wherein the at least one filler modifies one or more of an acoustic attenuation and a thermal conductivity of the porous matrix. In a third example of the system, optionally including one or both of the first and second examples, the phase change material transitions between a solid and a liquid, and wherein a phase change temperature of the phase change material is in a range of 30° C. to 50° C. In a fourth example of the system, optionally including one or more or each of the first through third examples, the one or more thermal management structures includes pores of the porous matrix, and wherein varying one or more of a pore shape, a pore size, a pore density, and a total porosity of the porous matrix varies a thermal conductivity of the porous matrix. In a fifth example of the system, optionally including one or more or each of the first through fourth examples, the one or more thermal management structures includes at least one support structure continuous and contiguous with the porous matrix, and wherein the at least one support structure and the porous matrix form a single integrated unit. In a sixth example of the system, optionally including one or more or each of the first through fifth examples, the at least one support structure includes one or more of an external wall, internal inclusions, and a heat sink, and wherein the at least one support structure is formed of a material with high thermal conductivity. In a seventh example of the system, optionally including one or more or each of the first through sixth examples, the internal inclusions are embedded in the porous matrix, and wherein the internal inclusions modify both an acoustic attenuation and a thermal conductivity of the porous matrix. In an eighth example of the system, optionally including one or more or each of the first through seventh examples, the porous matrix is formed of one of more of aluminum, aluminum nitride, copper, titanium, tungsten, a metal alloy, and stainless steel. In a ninth example of the system, optionally including one or more or each of the first through eighth examples, the additively manufactured backing is formed as a near-net shape, and wherein machining and/or grinding of the additively manufactured backing is minimized to achieve a net, final shape when the additively manufactured backing is formed as the near-net shape.

The disclosure also provides support for a method for manufacturing a transducer probe, comprising: additively manufacturing a backing with a nonhomogeneous structure for the transducer probe, the backing having at least one structural element providing one or more of a target acoustic attenuation and a target thermal conductivity. In a first example of the method, the target acoustic attenuation is at least 10 dB/mm at 3 MHz and the target thermal conductivity is at least 20 W/m·K. In a second example of the method, optionally including the first example, the target thermal conductivity is at least 40 W/m·K. In a third example of the method, optionally including one or both of the first and second examples when the at least one structural element provides the target thermal conductivity, the at least one structural element includes ports for filling and/or venting a porous matrix of the backing. In a fourth example of the method, optionally including one or more or each of the first through third examples, the at least one structural element includes pores of a porous matrix of the backing, an external wall continuously coupled to the porous matrix, one or more internal inclusions embedded in the porous matrix, and a heat sink continuously coupled to at least one of the external wall and the porous matrix. In a fifth example of the method, optionally including one or more or each of the first through fourth examples, the external wall at least partially surrounds the porous matrix and transfers heat around the porous matrix. In a sixth example of the method, optionally including one or more or each of the first through fifth examples, the one or more internal inclusions extend through the porous matrix along a signal propagation direction, and wherein varying a geometry, density, material, and orientation of the one or more internal inclusions modifies an acoustic attenuation and a thermal conductivity of the porous matrix.

The disclosure also provides support for a transducer probe, comprising: a piezoelectric layer for generating an acoustic signal, and a backing arranged below the piezoelectric layer, relative to a direction of signal propagation, and additively manufactured as a near-net shape, the near-net shape precluding subsequent machining or grinding to achieve a net shape, with at least one structural element moderating one or more of acoustic attenuation and thermal conductivity of the backing. In a first example of the system, the backing is additively manufactured with at least one internal cooling passage for flowing a coolant therethrough. In a second example of the system, optionally including the first example, the backing is a single, continuous unit including an attenuating domain, a heat storage domain, and a solid heat sink domain.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. An ultrasound probe, comprising:

an additively manufactured ultrasound probe backing having a porous matrix, the porous matrix at least partially filled with at least one filler, and one or more thermal management structures, wherein the additively manufactured ultrasound probe backing attenuates acoustic energy and enables a transfer of heat from a front of the probe to a rear of the ultrasound probe, wherein the one or more thermal management structures includes at least one support structure continuous and contiguous with the porous matrix, and wherein the at least one support structure and the porous matrix form a single integrated unit.

2. The ultrasound probe of claim 1, wherein the porous matrix has a nonhomogeneous structure, and wherein a uniformity, size, shape, and spacing of pores of the porous matrix is modified by varying one or more of a laser pass power, a print speed, a print direction, a print angle, a print hatching, and a print orientation during fabrication of the porous matrix.

3. The ultrasound probe of claim 1, wherein the at least one filler includes one or more of a lossy epoxy, a silicone, scattering particles, and a phase change material, and wherein the at least one filler modifies one or more of an acoustic attenuation and a thermal conductivity of the porous matrix.

4. The ultrasound probe of claim 3, wherein the phase change material transitions between a solid and a liquid, and wherein a phase change temperature of the phase change material is in a range of 30° C. to 50° C.

5. The ultrasound probe of claim 1, wherein the one or more thermal management structures includes pores of the porous matrix, and wherein varying one or more of a pore shape, a pore size, a pore density, and a total porosity of the porous matrix varies a thermal conductivity of the porous matrix.

6. The ultrasound probe of claim 1, wherein the one or more support structure includes an external wall, the external wall having a higher density and lower porosity than the porous matrix, and wherein the external wall is positioned between an acoustic stack and the porous matrix.

7. The ultrasound probe of claim 1, wherein the at least one support structure includes one or more of an external wall, internal inclusions, and a heat sink, and wherein the at least one support structure is formed of a material with high thermal conductivity.

8. The ultrasound probe of claim 7, wherein the internal inclusions are embedded in the porous matrix, and wherein the internal inclusions modify both an acoustic attenuation and a thermal conductivity of the porous matrix.

9. The ultrasound probe of claim 1, wherein the porous matrix is formed of one of more of aluminum, aluminum nitride, copper, titanium, tungsten, a metal alloy, and stainless steel.

10. The ultrasound probe of claim 1, wherein the additively manufactured ultrasound probe backing is formed as a near-net shape, and wherein machining and/or grinding of the additively manufactured ultrasound probe backing is minimized to achieve a net, final shape when the additively manufactured ultrasound probe backing is formed as the near-net shape.

* * * * *